(12) United States Patent
Shelton, IV et al.

(10) Patent No.: US 12,343,014 B2
(45) Date of Patent: Jul. 1, 2025

(54) SURGICAL INSTRUMENT WITH SELECTIVELY DISENGAGEABLE THREADED DRIVE SYSTEMS

(71) Applicant: Cilag GmbH International, Zug (CH)

(72) Inventors: Frederick E. Shelton, IV, Hillsboro, OH (US); Chester O. Baxter, III, Loveland, OH (US); Jerome R. Morgan, Cincinnati, OH (US); David C. Yates, Morrow, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 956 days.

(21) Appl. No.: 17/205,695

(22) Filed: Mar. 18, 2021

(65) Prior Publication Data

US 2021/0290233 A1   Sep. 23, 2021

Related U.S. Application Data

(63) Continuation of application No. 16/537,835, filed on Aug. 12, 2019, now Pat. No. 11,918,212, which is a
(Continued)

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 17/07292* (2013.01);
(Continued)

(58) Field of Classification Search
CPC ............ A61B 17/07207; A61B 17/068; A61B 17/07292; A61B 17/105; A61B 34/30;
(Continued)

(56) References Cited

U.S. PATENT DOCUMENTS 5,383,880 A * 1/1995 Hooven ............... A61B 17/072
606/213
5,403,312 A   4/1995 Yates et al.
(Continued)

FOREIGN PATENT DOCUMENTS

CN          204092074 U    1/2015

*Primary Examiner* — Robert F Long
*Assistant Examiner* — Mary C Hibbert-Copeland

(57) ABSTRACT

A surgical instrument including a surgical end effector and a threaded rotary input shaft. An actuator member is in operable engagement with the surgical end effector and is in selective threaded engagement with the threaded rotary input shaft such that when the actuator member is in an engaged configuration, rotation of said threaded rotary input shaft causes the actuator member to move axially to impart an actuation motion to the surgical end effector and when the actuator member is in a disengaged configuration, rotation of the threaded rotary input shaft will not be imparted to the actuator member. A switch may be employed for selectively moving the actuator between the engaged and disengaged configurations. A locking system may be employed for preventing axial movement of the actuator member when the actuator member is in the disengaged configuration.

15 Claims, 17 Drawing Sheets

Related U.S. Application Data continuation of application No. 14/674,915, filed on Mar. 31, 2015, now Pat. No. 10,433,844.

(51) Int. Cl.
| | | |
|---|---|---|
| *A61B 17/10* | (2006.01) | |
| *A61B 17/00* | (2006.01) | |
| *A61B 17/29* | (2006.01) | |
| *A61B 34/30* | (2016.01) | |
| *A61B 90/00* | (2016.01) | |

(52) U.S. Cl.
CPC .. *A61B 17/105* (2013.01); *A61B 2017/00017* (2013.01); *A61B 2017/00353* (2013.01); *A61B 2017/00367* (2013.01); *A61B 2017/00393* (2013.01); *A61B 2017/00398* (2013.01); *A61B 2017/00477* (2013.01); *A61B 2017/07235* (2013.01); *A61B 2017/07242* (2013.01); *A61B 2017/07257* (2013.01); *A61B 2017/07271* (2013.01); *A61B 2017/07278* (2013.01); *A61B 2017/07285* (2013.01); *A61B 2017/2903* (2013.01); *A61B 2017/2932* (2013.01); *A61B 2017/2936* (2013.01); *A61B 2017/2943* (2013.01); *A61B 34/30* (2016.02); *A61B 2090/034* (2016.02); *A61B 2090/061* (2016.02)

(58) Field of Classification Search
CPC ........ A61B 2090/034; A61B 2090/061; A61B 2017/00017; A61B 2017/00353; A61B 2017/00367; A61B 2017/00393; A61B 2017/00398; A61B 2017/00477; A61B 2017/07235; A61B 2017/07242; A61B 2017/07257; A61B 2017/07271; A61B 2017/07278; A61B 2017/07285; A61B 2017/2903; A61B 2017/2932; A61B 2017/2936; A61B 2017/2943
USPC ...................................... 227/176.1
See application file for complete search history.

(56) References Cited

U.S. PATENT DOCUMENTS

| | | |
|---|---|---|
| 5,433,721 A | 7/1995 | Hooven et al. |
| 5,667,517 A | 9/1997 | Hooven |
| 5,725,554 A | 3/1998 | Simon et al. |
| 5,762,255 A | 6/1998 | Chrisman et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,143,923 B2 | 12/2006 | Shelton, IV et al. |
| 7,398,908 B2 | 7/2008 | Holsten et al. |
| 7,422,139 B2 | 9/2008 | Shelton, IV et al. |
| 7,464,849 B2 | 12/2008 | Shelton, IV et al. |
| 7,500,979 B2 | 3/2009 | Hueil et al. |
| 7,635,074 B2 | 12/2009 | Olson et al. |
| 7,670,334 B2 | 3/2010 | Hueil et al. |
| 7,708,182 B2 | 5/2010 | Viola |
| 7,753,245 B2 | 7/2010 | Boudreaux et al. |
| 7,845,537 B2 | 12/2010 | Shelton, IV et al. |
| 7,980,443 B2 | 7/2011 | Scheib et al. |
| 8,210,411 B2 | 7/2012 | Yates et al. |
| 8,220,688 B2 | 7/2012 | Laurent et al. |
| 8,308,040 B2 | 11/2012 | Huang et al. |
| 8,393,514 B2 | 3/2013 | Shelton, IV et al. |
| 8,413,871 B2 | 4/2013 | Racenet et al. |
| 8,561,870 B2 | 10/2013 | Baxter, III et al. |
| 8,608,045 B2 | 12/2013 | Smith et al. |
| 8,733,613 B2 | 5/2014 | Huitema et al. |
| 9,072,535 B2 | 7/2015 | Shelton, IV et al. |
| 9,101,358 B2 | 8/2015 | Kerr et al. |
| 9,204,879 B2 | 12/2015 | Shelton, IV |
| 9,301,753 B2 | 4/2016 | Aldridge et al. |
| 9,307,986 B2 | 4/2016 | Hall et al. |
| 9,326,767 B2 | 5/2016 | Koch, Jr. et al. |
| 9,332,987 B2 | 5/2016 | Leimbach et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,398,911 B2 | 7/2016 | Auld |
| 9,445,816 B2 | 9/2016 | Swayze et al. |
| 9,468,438 B2 | 10/2016 | Baber et al. |
| 9,554,794 B2 | 1/2017 | Baber et al. |
| 9,603,599 B2 | 3/2017 | Miller et al. |
| 9,629,623 B2 | 4/2017 | Lytle, IV et al. |
| 9,629,629 B2 | 4/2017 | Leimbach et al. |
| 9,649,110 B2 | 5/2017 | Parihar et al. |
| 9,687,230 B2 | 6/2017 | Leimbach et al. |
| 9,690,362 B2 | 6/2017 | Leimbach et al. |
| 9,700,309 B2 | 7/2017 | Jaworek et al. |
| 9,724,094 B2 | 8/2017 | Baber et al. |
| 9,733,663 B2 | 8/2017 | Leimbach et al. |
| 9,737,301 B2 | 8/2017 | Baber et al. |
| 9,743,929 B2 | 8/2017 | Leimbach et al. |
| 9,750,499 B2 | 9/2017 | Leimbach et al. |
| 9,757,128 B2 | 9/2017 | Baber et al. |
| 9,782,169 B2 | 10/2017 | Kimsey et al. |
| 9,788,836 B2 | 10/2017 | Overmyer et al. |
| 9,801,626 B2 | 10/2017 | Parihar et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,814,460 B2 | 11/2017 | Kimsey et al. |
| 9,820,738 B2 | 11/2017 | Lytle, IV et al. |
| 9,826,976 B2 | 11/2017 | Parihar et al. |
| 9,826,977 B2 | 11/2017 | Leimbach et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,883,860 B2 | 2/2018 | Leimbach et al. |
| 9,888,919 B2 | 2/2018 | Leimbach et al. |
| 9,895,148 B2 | 2/2018 | Shelton, IV et al. |
| 9,901,342 B2 | 2/2018 | Shelton, IV et al. |
| 9,924,961 B2 | 3/2018 | Shelton, IV et al. |
| 9,931,118 B2 | 4/2018 | Shelton, IV et al. |
| 9,943,309 B2 | 4/2018 | Shelton, IV et al. |
| 9,968,355 B2 | 5/2018 | Shelton, IV et al. |
| 9,987,000 B2 | 6/2018 | Shelton, IV et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,501 B2 | 6/2018 | Shelton, IV et al. |
| 10,013,049 B2 | 7/2018 | Leimbach et al. |
| 10,016,199 B2 | 7/2018 | Baber et al. |
| 10,028,761 B2 | 7/2018 | Leimbach et al. |
| 10,045,776 B2 | 8/2018 | Shelton, IV et al. |
| 10,045,779 B2 | 8/2018 | Savage et al. |
| 10,052,044 B2 | 8/2018 | Shelton, IV et al. |
| 10,085,748 B2 | 10/2018 | Morgan et al. |
| 10,111,679 B2 | 10/2018 | Baber et al. |
| 10,117,649 B2 | 11/2018 | Baxter, III et al. |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,159,483 B2 | 12/2018 | Beckman et al. |
| 10,180,463 B2 | 1/2019 | Beckman et al. |
| 10,182,816 B2 | 1/2019 | Shelton, IV et al. |
| 10,188,385 B2 | 1/2019 | Kerr et al. |
| 10,201,364 B2 | 2/2019 | Leimbach et al. |
| 10,213,201 B2 | 2/2019 | Shelton, IV et al. |
| 10,226,250 B2 | 3/2019 | Beckman et al. |
| 10,245,027 B2 | 4/2019 | Shelton, IV et al. |
| 10,245,028 B2 | 4/2019 | Shelton, IV et al. |
| 10,245,033 B2 | 4/2019 | Overmyer et al. |
| 10,321,907 B2 | 6/2019 | Shelton, IV et al. |
| 10,390,825 B2 | 8/2019 | Shelton, IV et al. |
| 10,405,857 B2 | 9/2019 | Shelton, IV et al. |
| 10,433,844 B2 | 10/2019 | Shelton, IV et al. |
| 10,441,279 B2 | 10/2019 | Shelton, IV et al. |

(56) References Cited

U.S. PATENT DOCUMENTS

| | | | |
|---|---|---|---|
| 10,470,762 B2 | 11/2019 | Leimbach et al. | |
| 10,517,594 B2 | 12/2019 | Shelton, IV et al. | |
| 10,548,504 B2 | 2/2020 | Shelton, IV et al. | |
| 10,617,412 B2 | 4/2020 | Shelton, IV et al. | |
| 10,687,806 B2 | 6/2020 | Shelton, IV et al. | |
| 11,141,153 B2 | 10/2021 | Shelton, IV et al. | |
| 11,918,212 B2 | 3/2024 | Shelton, IV et al. | |
| 2007/0175955 A1 | 8/2007 | Shelton et al. | |
| 2009/0101692 A1* | 4/2009 | Whitman | A61B 90/98 227/175.1 |
| 2014/0005676 A1* | 1/2014 | Shelton, IV | A61B 17/062 606/130 |
| 2014/0246475 A1 | 9/2014 | Hall et al. | |
| 2014/0249557 A1 | 9/2014 | Koch, Jr. et al. | |
| 2014/0263541 A1 | 9/2014 | Leimbach et al. | |
| 2014/0263552 A1 | 9/2014 | Hall et al. | |
| 2014/0309665 A1* | 10/2014 | Parihar | A61B 17/282 606/139 |
| 2015/0272557 A1 | 10/2015 | Overmyer et al. | |
| 2015/0272571 A1 | 10/2015 | Leimbach et al. | |
| 2015/0272580 A1 | 10/2015 | Leimbach et al. | |
| 2015/0272582 A1 | 10/2015 | Leimbach et al. | |
| 2016/0066913 A1 | 3/2016 | Swayze et al. | |
| 2016/0174969 A1 | 6/2016 | Kerr et al. | |
| 2016/0174983 A1 | 6/2016 | Shelton, IV et al. | |
| 2016/0249910 A1 | 9/2016 | Shelton, IV et al. | |
| 2016/0256184 A1 | 9/2016 | Shelton, IV et al. | |

* cited by examiner

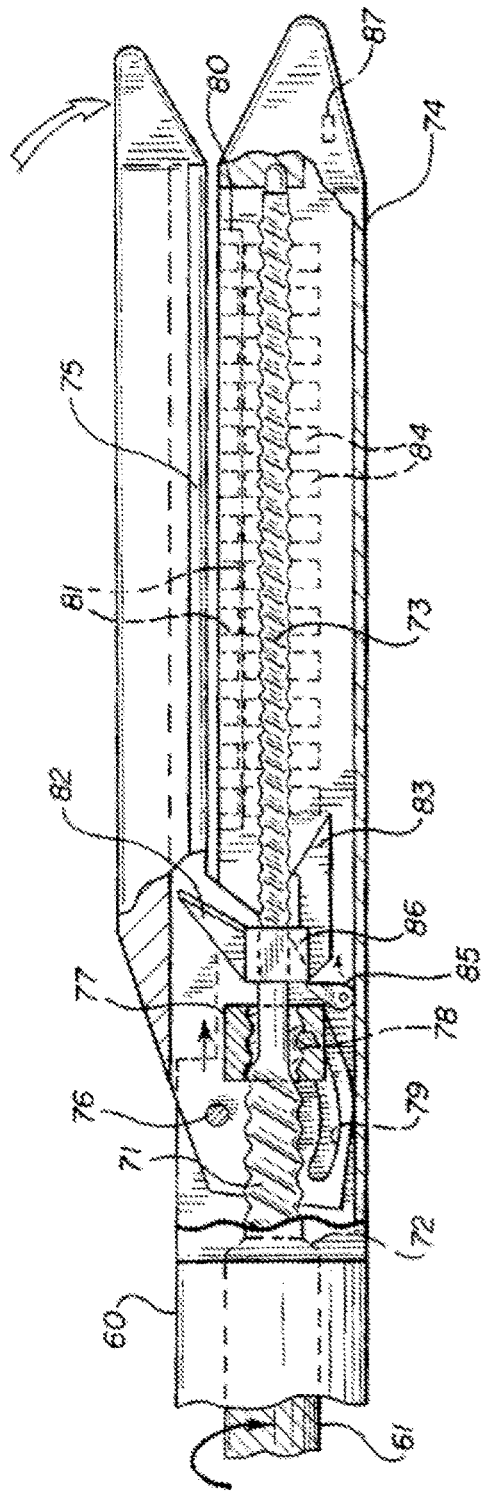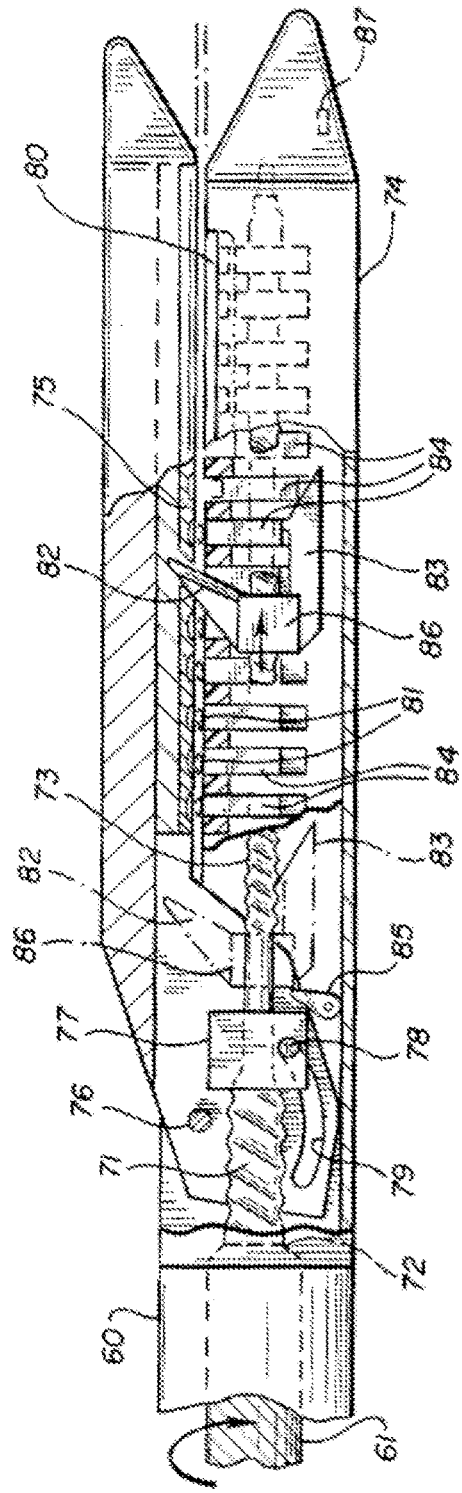

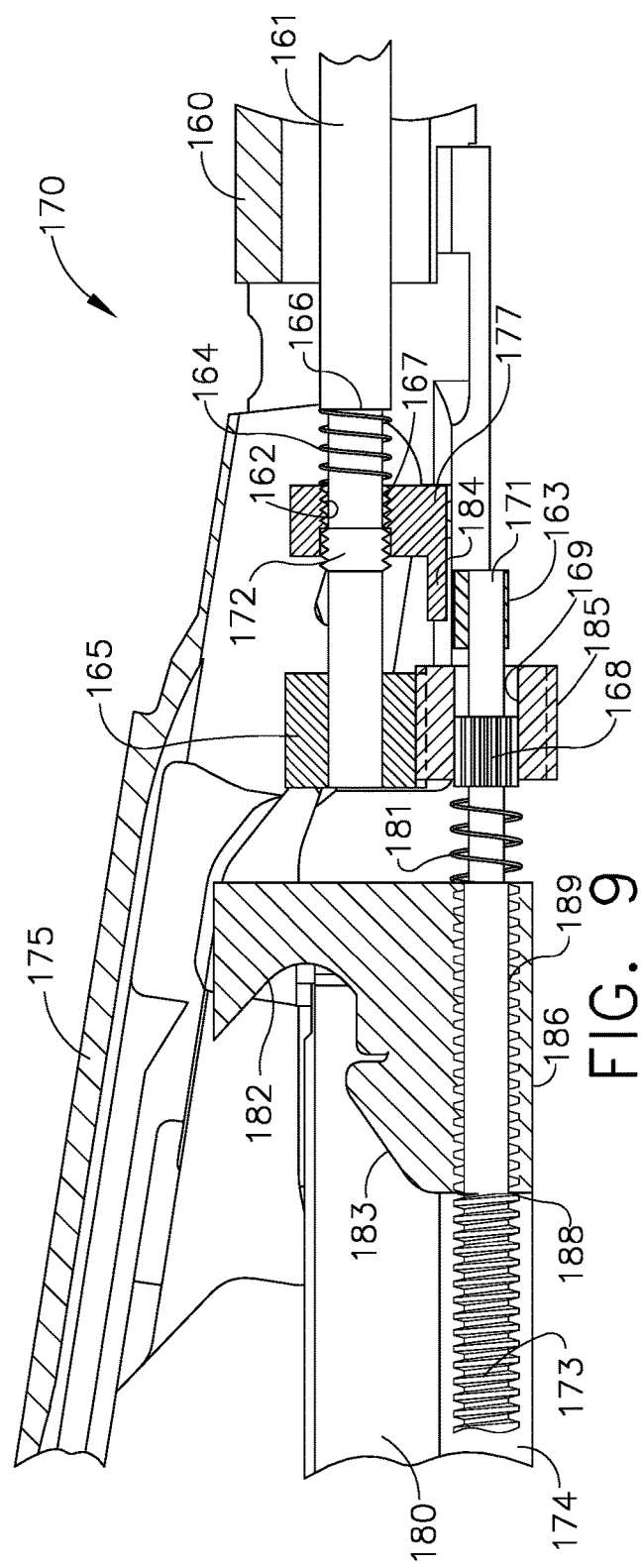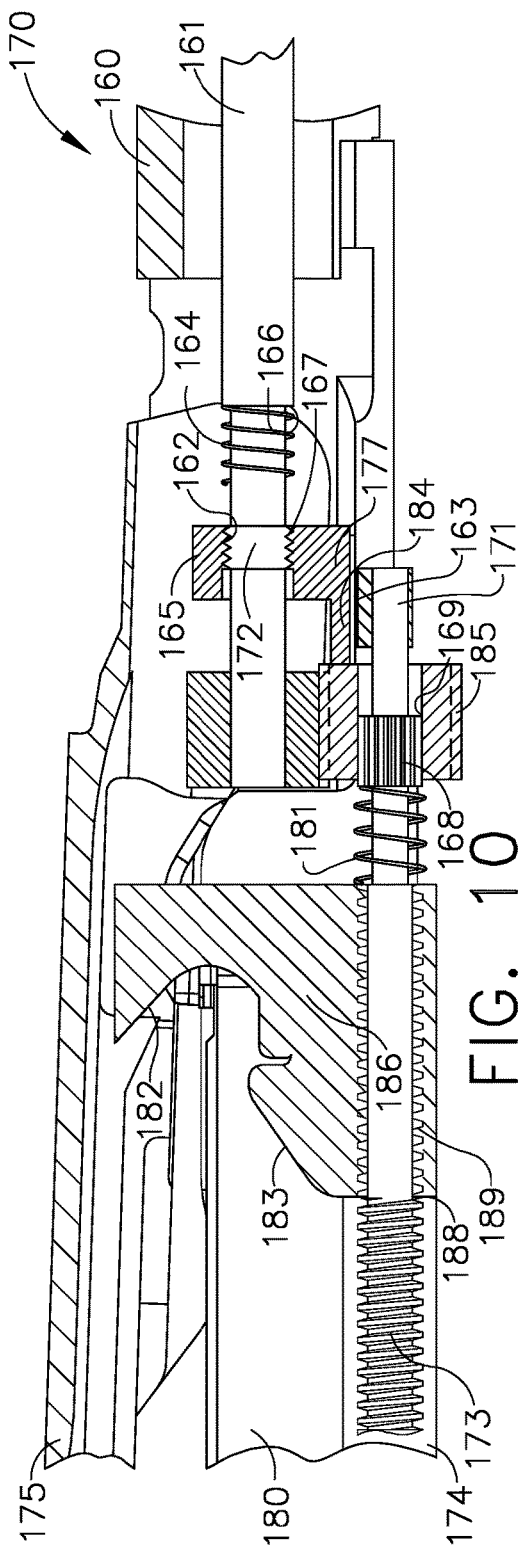

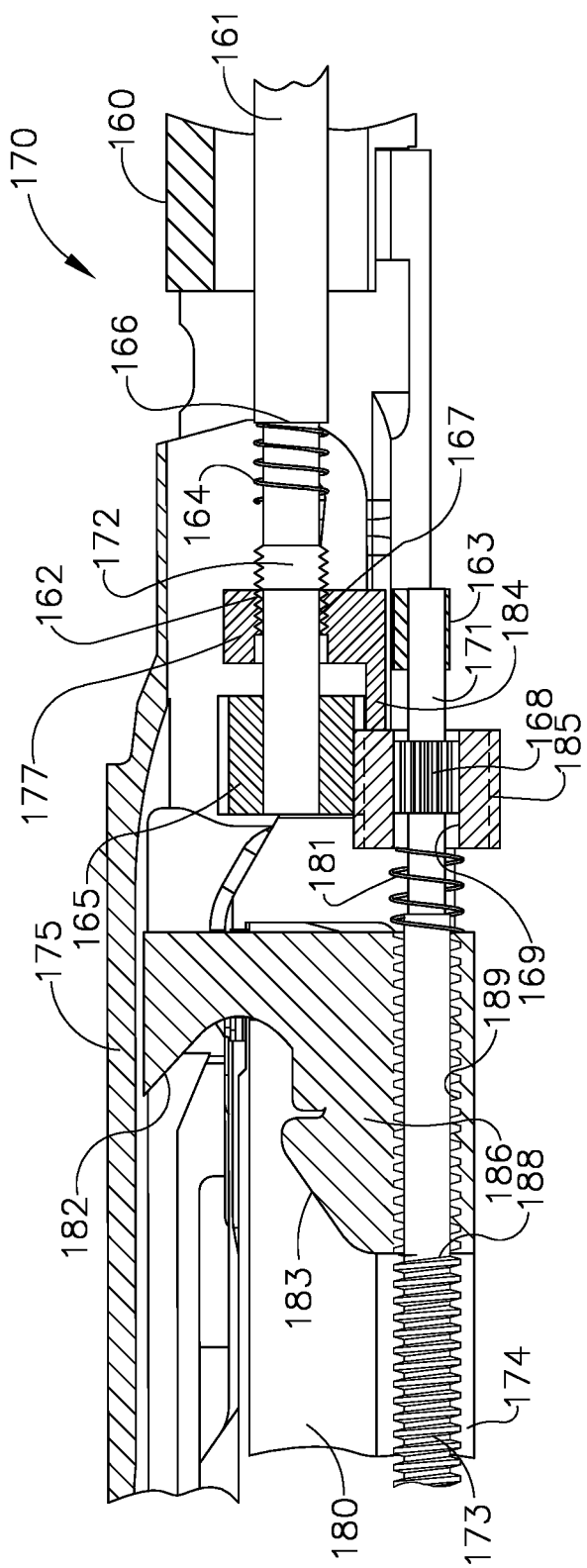
FIG. 11
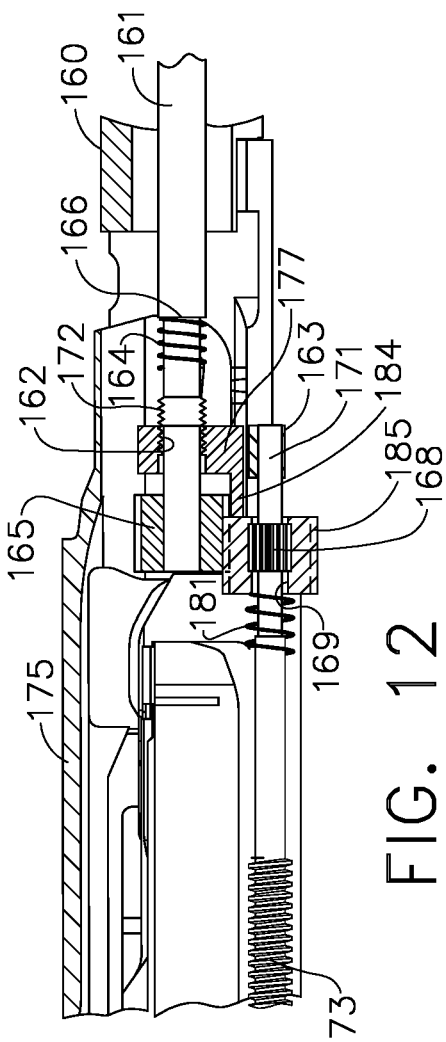
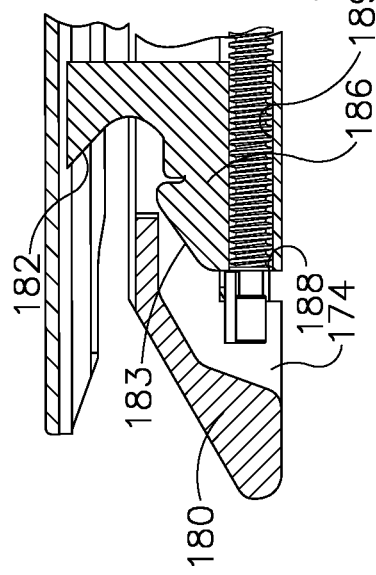
FIG. 12

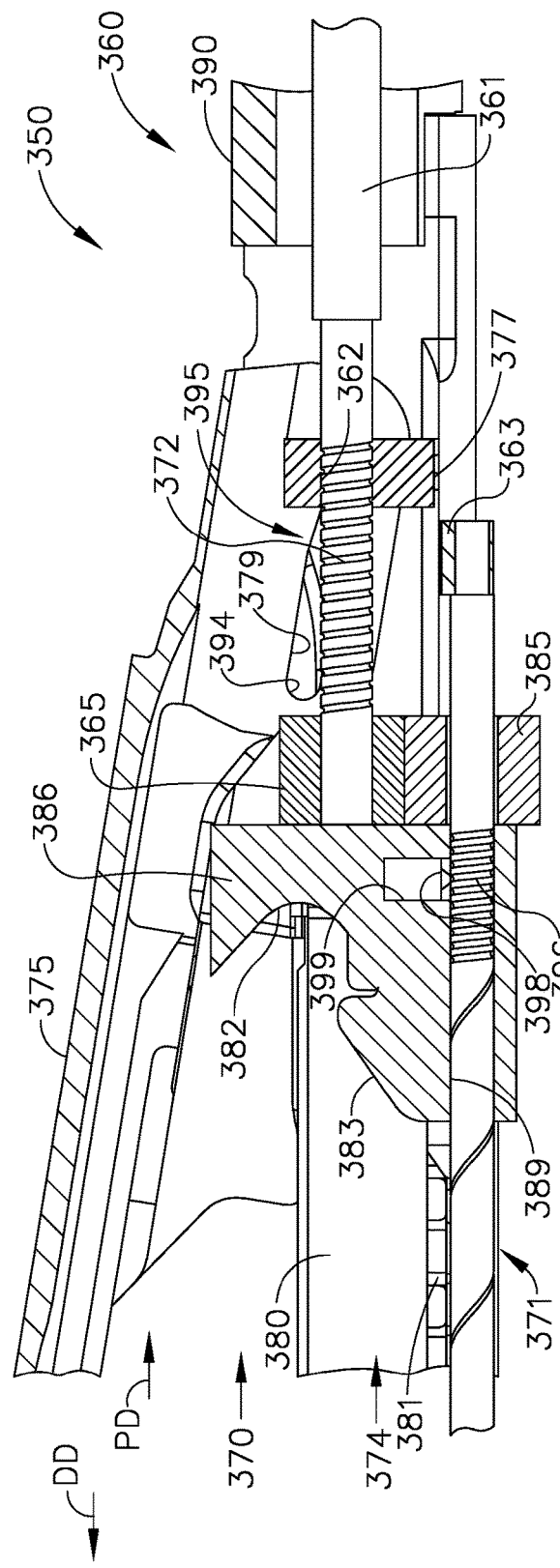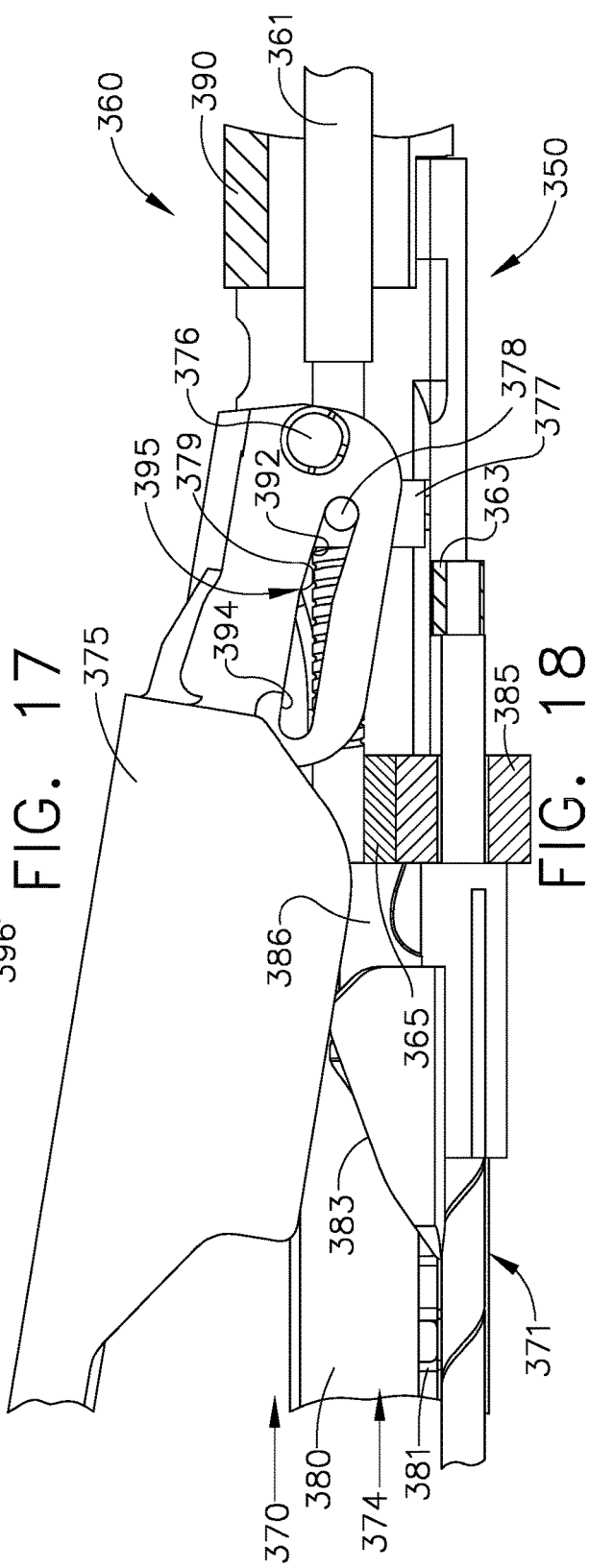

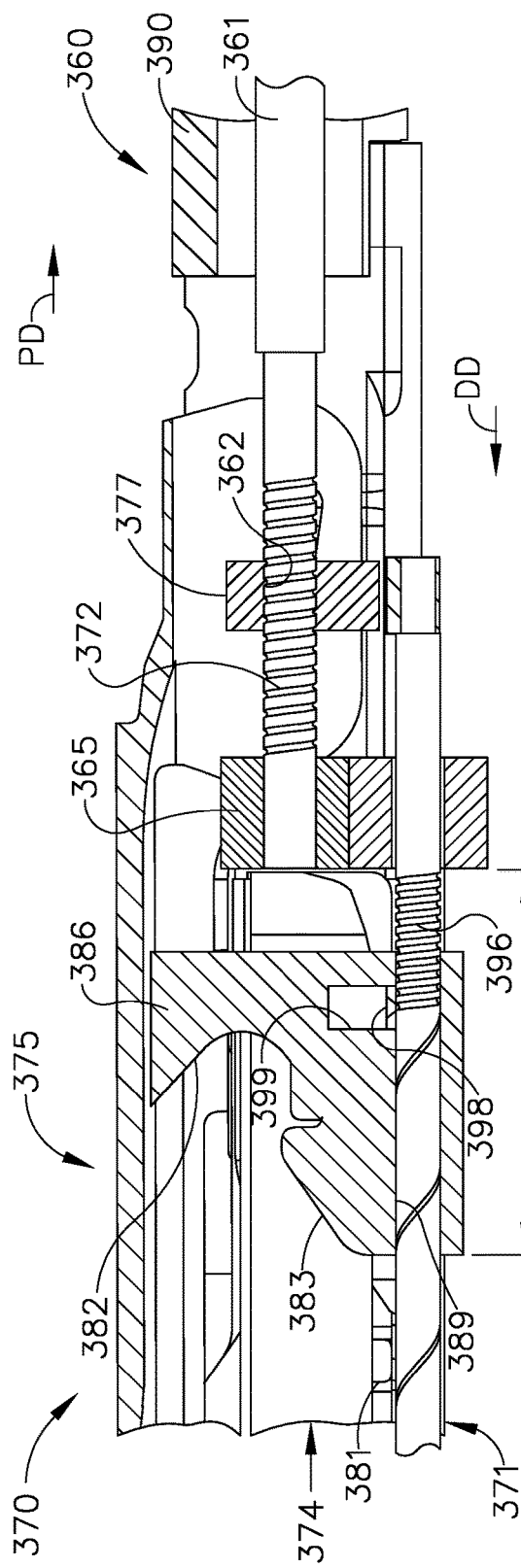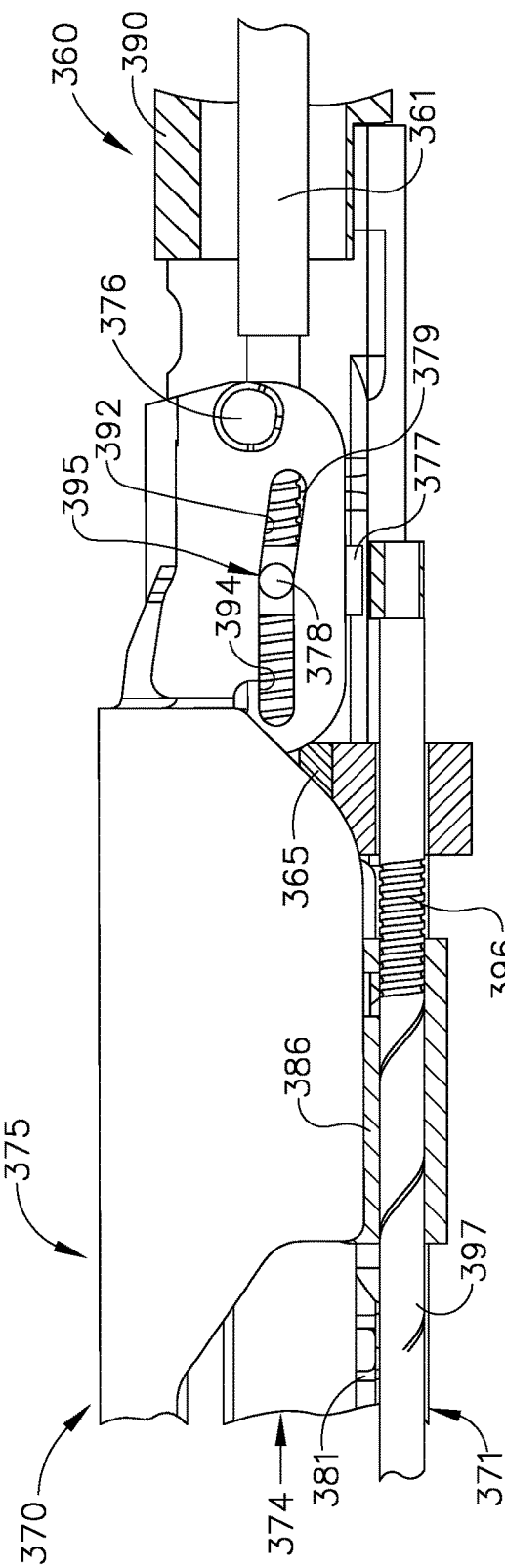

US 12,343,014 B2

SURGICAL INSTRUMENT WITH SELECTIVELY DISENGAGEABLE THREADED DRIVE SYSTEMS

CROSS-REFERENCE TO RELATED APPLICATIONS

This application is a continuation application that claims priority under 35 U.S.C. § 120 to U.S. patent application Ser. No. 16/537,835, filed Aug. 12, 2019, entitled SURGICAL INSTRUMENT WITH SELECTIVELY DISENGAGEABLE DRIVE SYSTEMS, which issued on Mar. 5, 2024 as U.S. Pat. No. 11,918,212, which is a continuation application that claims priority under 35 U.S.C. § 120 to U.S. patent application Ser. No. 14/674,915, filed Mar. 31, 2015, entitled SURGICAL INSTRUMENT WITH SELECTIVELY DISENGAGEABLE THREADED DRIVE SYSTEMS, which issued on Oct. 8, 2019 as U.S. Pat. No. 10,433,844, the entire disclosures of which are hereby incorporated by reference herein.

BACKGROUND

The present invention relates to surgical instruments and, in various embodiments, to surgical stapling and cutting instruments and staple cartridges for use therewith.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows.

The foregoing discussion is intended only to illustrate various aspects of the related art in the field of the invention at the time, and should not be taken as a disavowal of claim scope.

BRIEF DESCRIPTION OF THE DRAWINGS

Various features of the embodiments described herein, together with advantages thereof, may be understood in accordance with the following description taken in conjunction with the accompanying drawings as follows:

FIG. 2 is a longitudinal cross-sectional view of the end effector of FIG. 1 illustrated in a closed, or clamped, configuration and illustrating a firing member in a pre-fired position prior to firing the staples;

FIG. 3 is a longitudinal cross-sectional view of the end effector of FIG. 1 illustrating a firing member of the end effector in a partially-fired position;

FIG. 9 is another partial cross-sectional elevational view of the end effector of FIG. 6 illustrating a closure system of the end effector in an open configuration and a firing system of the end effector in an unfired configuration;

FIG. 10 is a partial cross-sectional elevational view of the end effector of FIG. 6 illustrating the closure system in a partially closed configuration and the firing system in an unfired configuration;

FIG. 11 is a partial cross-sectional elevational view of the end effector of FIG. 6 illustrating the closure system in a fully closed configuration and the firing system in a partially fired configuration;

FIG. 12 is a partial cross-sectional elevational view of the end effector of FIG. 6 illustrating the closure system in a fully closed configuration and the firing system in a fully fired configuration;

FIG. 17 is a longitudinal cross-sectional view of a portion of the end effector of FIG. 16 with a portion of the anvil shown in cross-section and illustrated in an open position with the closure nut thereof in a beginning position and with the firing nut shown in a starting pre-fired position;

FIG. 18 is another longitudinal cross-sectional view of the end effector of FIG. 17 with the anvil portion shown in full view;

FIG. 19 is another longitudinal cross-sectional view of a portion of the end effector of FIG. 17 with a portion of the anvil shown in cross-section and with the closure nut in the "intermediate" fully-closed position and the firing nut in a pre-fired position located at the distal end of the neutral firing range;

FIG. 20 is another longitudinal cross-sectional view of a portion of the end effector of FIG. 19 with the anvil portion shown in full view;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
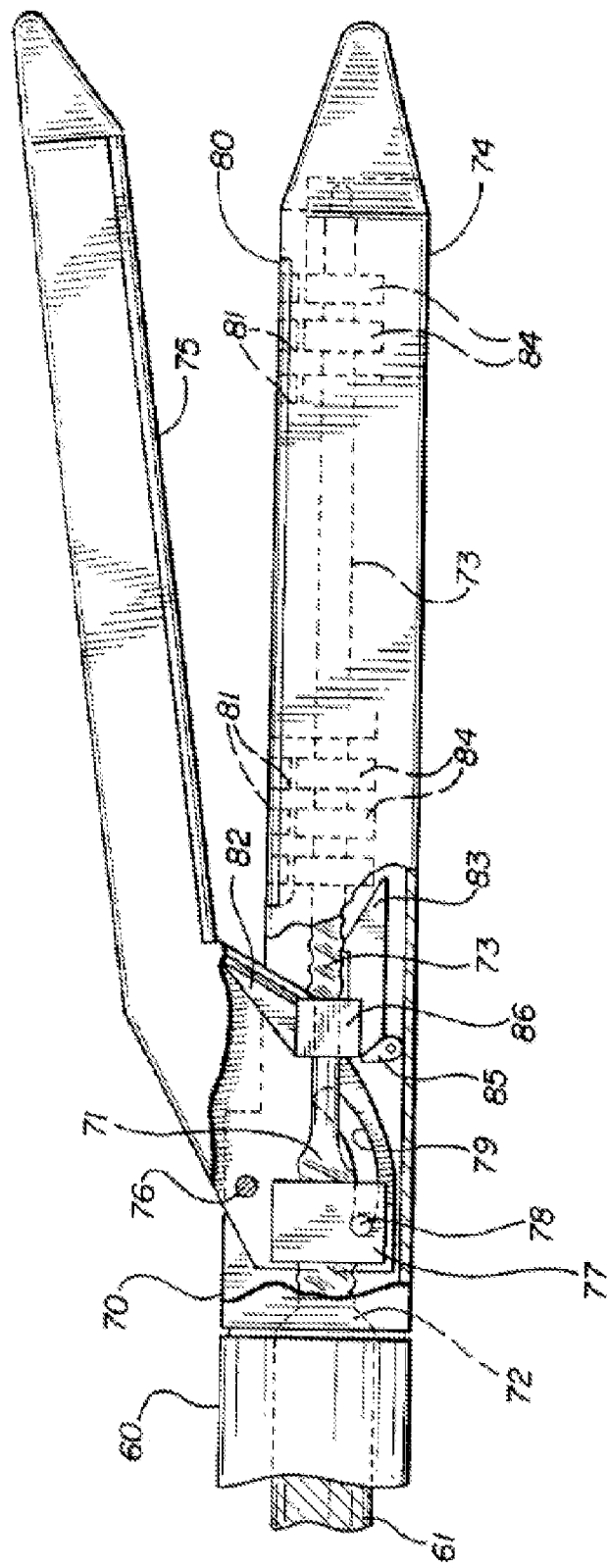
FIG. 1 is a longitudinal cross-sectional view of an end effector of a surgical instrument system illustrated in an open, or unclamped, configuration which includes a staple cartridge, staples removably stored in the staple cartridge, and an anvil configured to deform the staples.
Figure 4:
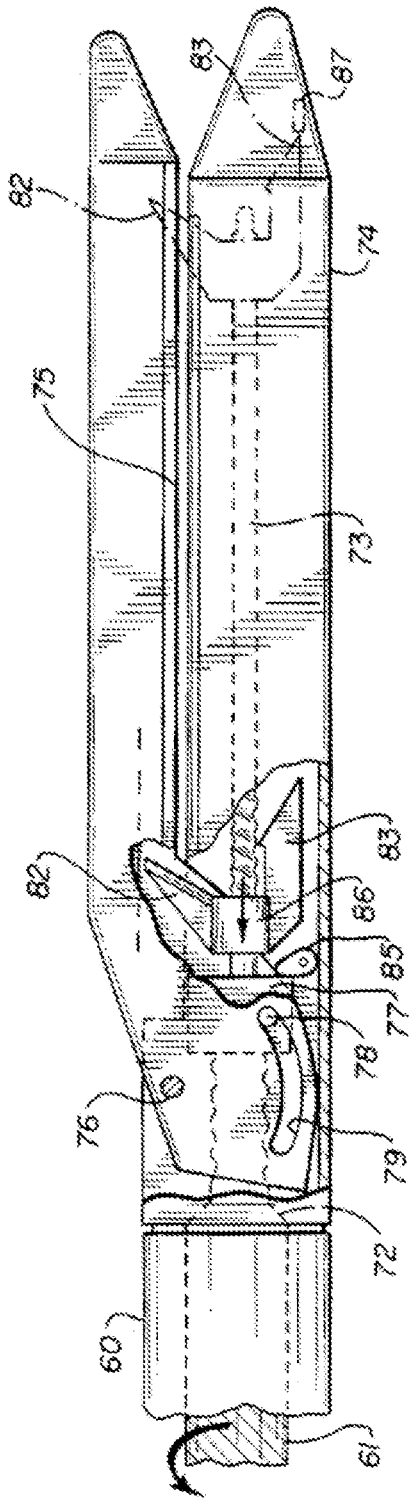
FIG. 4 is a longitudinal cross-sectional view of the end effector of FIG. 1 illustrating the firing member in a retracted position.
Figure 5:
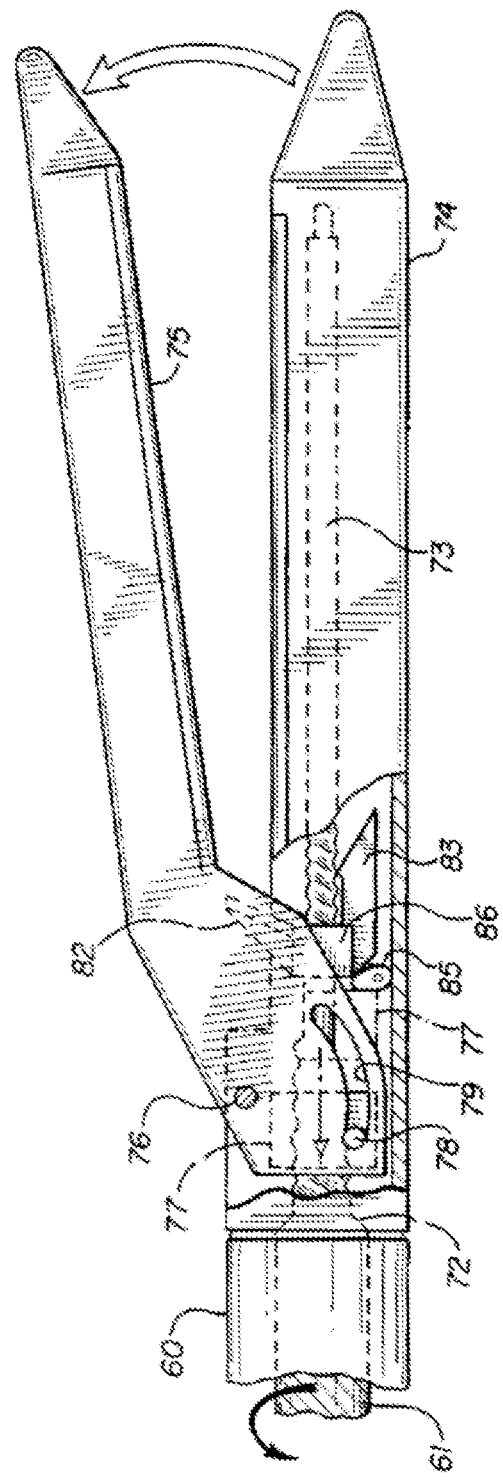
FIG. 5 is a longitudinal cross-sectional view of the end effector of FIG. 1 illustrating the end effector in a re-opened configuration.

Applicant of the present application owns the following patent applications that were filed on Mar. 31, 2015 and which are each herein incorporated by reference in their respective entireties:

U.S. patent application Ser. No. 14/675,008, entitled STAPLING END EFFECTOR CONFIGURED TO COMPENSATE FOR AN UNEVEN GAP BETWEEN A FIRST JAW AND A SECOND JAW, now U.S. Pat. No. 10,213,201; and U.S. patent application Ser. No. 14/674,965, entitled SURGICAL INSTRUMENT WITH PROGRESSIVE ROTARY DRIVE SYSTEMS, now U.S. Pat. No. 10,390,825.

Applicant of the present application owns the following patent applications that were filed on Mar. 6, 2015 and which are each herein incorporated by reference in their respective entireties:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Pat. No. 10,687,806;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Pat. No. 10,548,504;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLER, now U.S. Pat. No. 10,617,412;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entireties:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S.

Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled USE OF POLARITY OF HALL MAGNET DETECTION TO DETECT MISLOADED CARTRIDGE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Pat. No. 9,844,368;

U.S. patent application Ser. No. 14/248,588, entitled POWERED LINEAR SURGICAL STAPLER, now U.S. Pat. No. 10,405,857;

U.S. patent application Ser. No. 14/248,591, entitled TRANSMISSION ARRANGEMENT FOR A SURGICAL INSTRUMENT, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR; U.S. Provisional Patent Application Ser. No. 61/812,376, entitled LINEAR-CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIGS. 1-5 are longitudinal cross-sectional views of an end effector of a surgical instrument system. The views depict the end effector in an open position prior to being placed onto tissue (FIG. 1), in a closed position ready for firing (FIG. 2), during a firing action to deploy staples into the tissue (FIG. 3), after the firing action has been completed (FIG. 4), and in a re-opened position (FIG. 5) to release the end effector from the tissue. This surgical instrument system is similar in many respects to the surgical instrument system disclosed in U.S. Pat. No. 5,667,517, entitled ENDOSCOPIC SURGICAL SYSTEM WITH SENSING MEANS, which issued on Sep. 16, 1997 to Michael Dawson Hooven. The entire disclosure of U.S. Pat. No. 5,667,517 is incorporated by reference herein.

The end effector of FIGS. 1-5 includes a shaft housing 60 and an end effector housing 70. The end effector housing 70 is connected to the shaft housing 60 in any suitable manner, such as by a press fit or ultrasonic welding, for example. A rotatable shaft 61 extends through the shaft housing 60 and is operably coupled with an electric motor, for example, which can rotate the shaft 61. A threaded rod 71 extends substantially the length of the end effector and is connected to the rotatable shaft 61. The threaded rod 71 has a larger diameter portion 72 adjacent the shaft 61 and a smaller diameter portion 73 for the remainder of the threaded rod 71. The end effector further includes a staple or staple cartridge portion 74 and an anvil portion 75. The staple cartridge portion 74 and the anvil portion 75 are pivotally connected to each other by the anvil pivot pin 76. Threadably mounted on the larger diameter portion 72 of the threaded rod 71 is a closure nut 77 and extending from that closure nut 77 is a closure pin 78 which moves in a closure slot 79 disposed in the pivotally mounted anvil portion 75 of the end effector. When the shaft 61 is rotated, the threaded rod 71 is also rotated and, upon the rotation thereof in a first direction, the closure nut 77 will move down the threaded rod 71 and move the closure pin 78 in the closure slot 79 to close the anvil portion 75 against the staple portion 74 of the end effector.

Further to the above, the tissue to be treated or manipulated by the end effector is placed between the anvil portion 75 and the staple cartridge portion 74 of the end effector when the anvil portion 75 is in its open position. Once the tissue has been suitably positioned between the anvil portion 75 and the staple cartridge portion 74, power is applied to the shaft 61 to rotate the shaft 61 and the threaded rod 71 and close the anvil portion 75. As can be appreciated, the amount of torque required to pivot the anvil portion 75 about the pivot pin 76 can be sensed and, as a result, the thickness of tissue between the anvil portion 75 and the staple cartridge portion 74 can be determined. The surgical instrument system can further include a microprocessor, or controller, which can manipulate this information and inform the surgeon as to whether or not an appropriate amount of tissue is positioned between the anvil portion 75 and the staple cartridge portion 74 of the end effector upon closing the anvil portion 75 or whether too much or too little tissue is positioned between the anvil portion 75 and the staple cartridge portion 74. The microprocessor can also be configured to indicate to the surgeon whether or not the end effector should be re-manipulated. When the electric motor rotating the shaft 61 is driven by a constant voltage, for example, the force required to close the end effector may be measured by monitoring the motor current. In various instances, the power delivered to the end effector may be controlled by varying the motor voltage and/or current to achieve a constant motor speed with varying load, for example. In certain instances, pulse width modulation and/or frequency modulation may be utilized to control the electric motor.

The staple cartridge portion 74 comprises a removable staple cartridge 80. The staple cartridge 80 can include any suitable number of staple rows, such as four rows of staples 81 or six rows of staples 81, for example. The staple rows are parallel to one another and, in adjacent rows, are off-set with respect to one another. The staple cartridge 80 is placed in the staple cartridge portion 74 so that it is opposite the anvil portion 75 and snaps into the staple cartridge portion 74 of the end effector as shown. As depicted in FIGS. 1-5, the smaller diameter portion 73 of the threaded rod 71 extends through the staple cartridge 80. The staple cartridge 80 can include an opening defined in the bottom thereof which permits the staple cartridge 80 to be positioned over the threaded rod 71 and seated into position in the staple cartridge portion 74. Other embodiments are envisioned in which the threaded rod 71, or at least a portion of the threaded rod 71, is part of the staple cartridge 80. In such an embodiment, the threaded rod 71 can be operably coupled with the drive shaft 61 when the staple cartridge 80 is seated in the staple cartridge portion 74. Some embodiments are envisioned in which the staple cartridge 80 is not readily replaceable within the end effector. In at least one such embodiment, the end effector, as a whole, may be replaceable.

Mounted on the threaded rod 71 is a knife member 82 and a driving wedge member 83 which are interconnected. The interconnected knife member 82 and wedge member 83 are threadably engaged with the smaller diameter portion 73 of the threaded rod 71 and are advanced distally when the threaded rod 71 is rotated in the first direction, i.e., the same direction in which the threaded rod 71 is rotated to close the anvil portion 75. The wedge member 83 precedes, or is positioned distally with respect to, the knife member 82 as they move along the threaded rod 71. As the wedge member 83 moves down the threaded rod 71, the wedge member 83 drives the staples 81 out of the cartridge 80 via staple drivers 84. The staple drivers 84 can comprise individual staple drivers or, alternatively, one or more of the staple drivers 84 can be interconnected. The staples 81 pass through the tissue and are pushed against the anvil portion 75 to form the staples 81 in the tissue. The knife member 82 following the driving wedge 83 cuts the tissue between two adjacent rows of staples 81. The driving wedge 83 can be comprised of two portions; that is, it has one wedge piece on one side of the knife member 82 to drive the staples 81 on a first side of the knife member 82 and a like wedge piece on the opposite side of the knife member 82 to drive the staples 81 on a second, or opposite, side of the knife member 82.

The staples 81 have the same unformed heights; however, it is envisioned that the staples 81 can have different unformed heights. The staples 81 have the same deformed heights; however, it is envisioned that the staples 81 can have different deformed heights. The entire disclosure of U.S. Patent Application Publication No. 2007/0131732, entitled SURGICAL STAPLING INSTRUMENTS INCLUDING A CARTRIDGE HAVING MULTIPLE STAPLE SIZES, now U.S. Pat. No. 7,398,908, which was filed on Nov. 3, 2006, is incorporated by reference herein. The entire disclosure of U.S. Pat. No. 7,635,074, entitled STAPLE DRIVE ASSEMBLY, which issued on Dec. 22, 2009, is incorporated by reference herein. The entire disclosures of U.S. patent application Ser. No. 14/527,398, entitled STAPLE CARTRIDGES COMPRISING DRIVER ARRANGEMENTS, which was filed on Oct. 29, 2014, and U.S. patent application Ser. No. 14/527,384, entitled CARTRIDGE ASSEMBLIES FOR SURGICAL STAPLERS, which was filed on Oct. 29, 2014, are incorporated by reference herein.

When the anvil portion 75 is closed as shown in FIG. 2, the closure nut 77 moves a stop member 85 forward so that the firing nut 86 on which the knife 82 and wedges 83 are disposed is moved forward and engages the threads of the smaller diameter portion 73 of the threaded rod 71 to move forward along the rod 71 and drive the staples 81 and cut the tissue. Concurrent with the closure nut 77 switching the stop member 85 from its rearward facing configuration (FIG. 6) to its forward facing configuration (FIG. 7), the closure nut 77 runs off of, or disengages from, the thread of the threaded portion 72. The firing nut 86 is biased, using a suitable means, so as not to engage the thread of the threaded portion 73 until the stop member 85 is activated, or pushed forward, as described above. Once the firing nut 86 has been moved to its most-forward position to drive and form all of the staples 81 and cut the tissue, the firing nut 86 engages a suitable contact 87 which immediately reverses the electric motor to rotate the rod in a second, or opposite direction, to retract the firing nut 86. In its fully retracted position, referring now to FIG. 9, the firing nut 86 moves the stop member 85 rearwardly causing the closure nut 77 to become re-engaged with the thread of the threaded portion 72. Concurrent with the stop member 85 being pushed into its rearward facing configuration (FIG. 9), the firing nut 86 runs off of, or disengages from, the thread of the threaded portion 73. The continued rotation of the threaded rod 71 in the second direction retracts the closure nut 77 and opens the anvil portion 75 of the end effector, as illustrated in FIG. 10.

Another configuration of the above-described embodiments would be to locate contacts in a handle portion of the instrument, or a proximal housing that is attached to a robotic surgical stapler, and use a follower nut on the rotating shaft 61 to monitor the position of the closure nut 77 and/or the firing nut 86. The entire disclosure of U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, is incorporated by reference herein. Various information may be transmitted to and/or from the microprocessor of the surgical instrument system during the operation thereof; for example, the movement of the stop member 85 pushing the firing nut 86 onto the thread of the threaded portion 73 and/or pushing the closure nut 77 onto the thread of the threaded portion 72 can be sensed. The most forward position of the wedges 83 and/or knife member 82 may be sensed. The reversal of the motor may also be sensed. Furthermore, the presence of a staple cartridge 80 in the staple cartridge portion 74 and/or the presence of staples 81 in that cartridge 80 may also be sensed. All of this information may be fed back to the controller and stored and manipulated in the controller so that the surgeon using the instrument can receive information regarding the condition of the surgical instrument system.

The surgical instrument systems disclosed herein can be utilized with an adjunct material, such as buttress material, for example. The adjunct material can comprise one or more layers of material releasably attached to the staple cartridge and/or the anvil. The entire disclosure of U.S. Patent Application Publication 2010/0012704, entitled SURGICAL STAPLING APPARATUS, which published on Jan. 21, 2010, now U.S. Pat. No. 8,413,871, is incorporated by reference herein.

The surgical instrument system depicted in FIGS. 1-5 and described above is useful for its intended purpose; however, there are several aspects of this surgical instrument system that can be improved. For instance, the closure nut 77 and the firing nut 86 are advanced sequentially. Stated another way, the closure nut 77 completes its entire closing stroke on the threaded portion 72 of the rod 71 before the firing nut 86 begins its firing stroke on the threaded portion 73 of the rod 71. As a result, the tissue clamping system must be fully clamped before the staple firing system can be operated. Moreover, the firing nut 86 must be completely retracted before the closure nut 77 can be retracted. As a result, the tissue clamping system cannot be unclamped immediately after the staples 81 have been fired; rather, the tissue clamping system is stuck in its clamped configuration until the firing system has been completely reset. In addition to the above, coordinating the disengagement of the closure nut 77 from the thread of the threaded portion 72 at the same time that the closure nut 77 switches the stop member 85 to its forward-facing configuration may require very precise tolerances. Similarly, coordinating the disengagement of the firing nut 86 from the thread of the threaded portion 73 at the same time that the firing nut 86 switches the stop member 85 to its rearward-facing configuration may also require very precise tolerances.

A surgical instrument system 150 is illustrated in FIGS. 6-14. The surgical instrument system 150 includes a shaft 160 and an end effector 170 extending from the shaft 160. The shaft 160 extends from a housing 152 which is configured to be attached to a robotic surgical system, such as the DAVINCI robotic surgical system manufactured by Intuitive Surgical, Inc., for example. The entire disclosure of U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535 is incorporated by reference herein. Alternatively, the shaft 160 can extend from a handle of a surgical instrument configured to be grasped and operated by a surgeon, for example. The entire disclosures of U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, are incorporated by reference herein. The shaft 160 comprises at least one articulation joint, such as articulation joint 190, for example, which is configured to permit the end effector 170 to be articulated about at least one axis of rotation. Other embodiments are envisioned in which the shaft 160 does not comprise an articulation joint.

Figure 6:
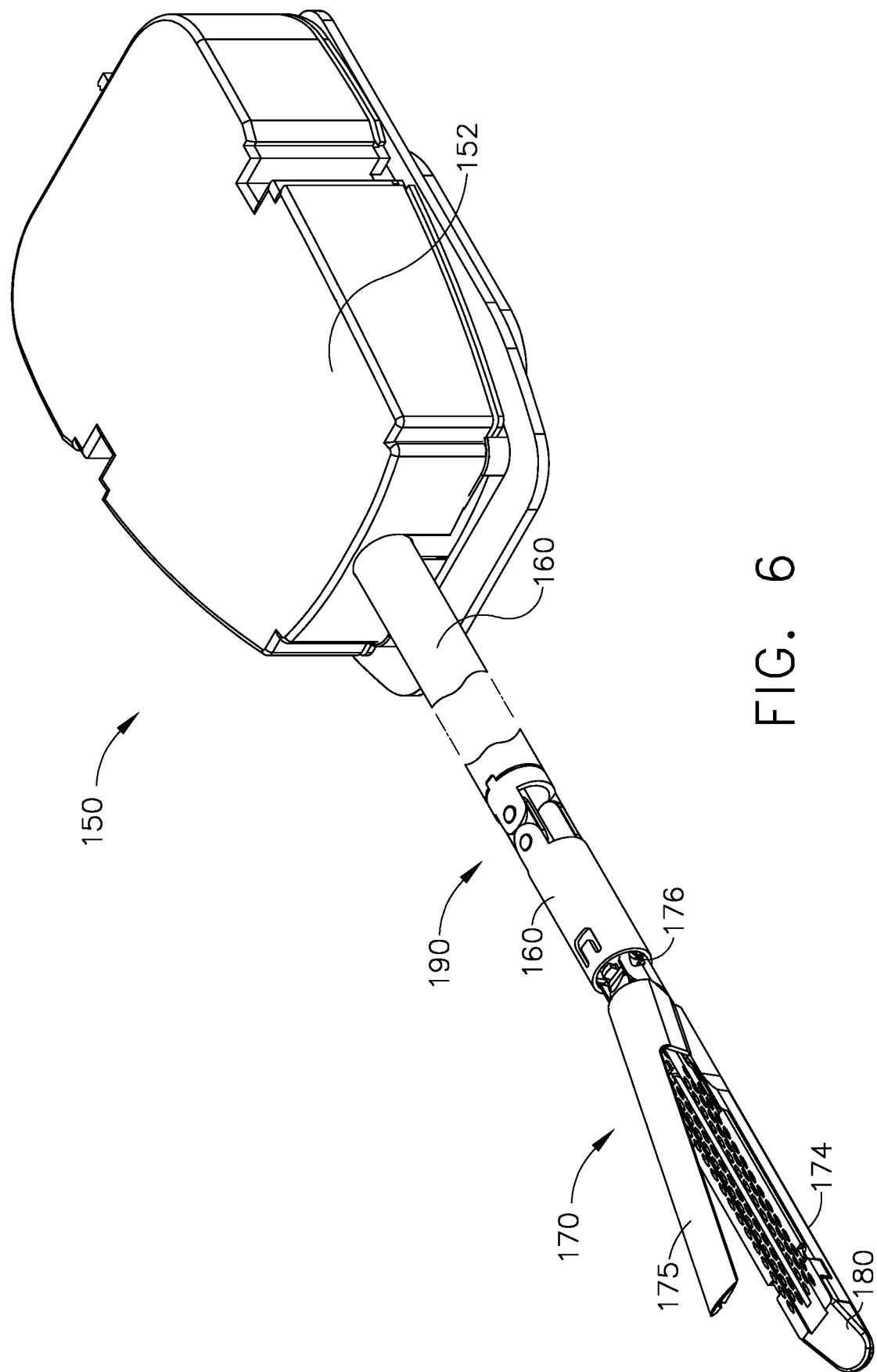
FIG. 6 is a perspective view of a surgical stapling system comprising an end effector in accordance with at least one embodiment.

Referring primarily to FIG. 6, the end effector 170 comprises a staple cartridge portion 174 and an anvil portion 175. A staple cartridge 180 is positioned in the staple cartridge portion 174. The staple cartridge 180 is removable from the staple cartridge portion 174 such that it can be readily replaced with another staple cartridge; however, other embodiments are envisioned in which the staple cartridge 180 is not readily replaceable. The anvil portion 175 is rotatable relative to the staple cartridge portion 174 about pivot pins 176 extending from the anvil portion 175. Alternative embodiments are envisioned in which the staple cartridge portion 174 is rotatable relative to the anvil portion 175. The anvil 175 is rotatable between an open position (FIGS. 6-9) and a closed position (FIGS. 10-13) by a closure drive as described in greater detail further below. Staples, such as staples 81, for example, are removably stored in the staple cartridge 180 and can be ejected from the staple cartridge 180 by a firing drive and deformed against the anvil 175, as also described in greater detail further below.

Figure 7:
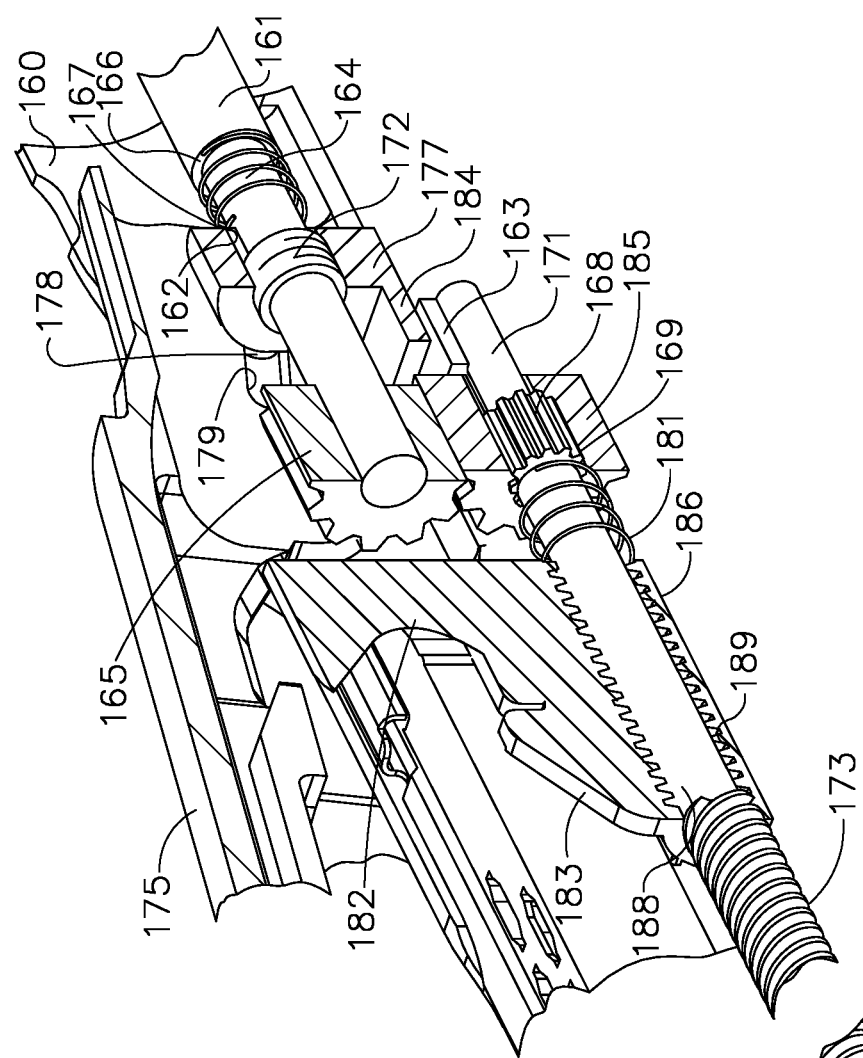
FIG. 7 is a partial cross-sectional perspective view of the end effector of FIG. 6.
Figure 8:
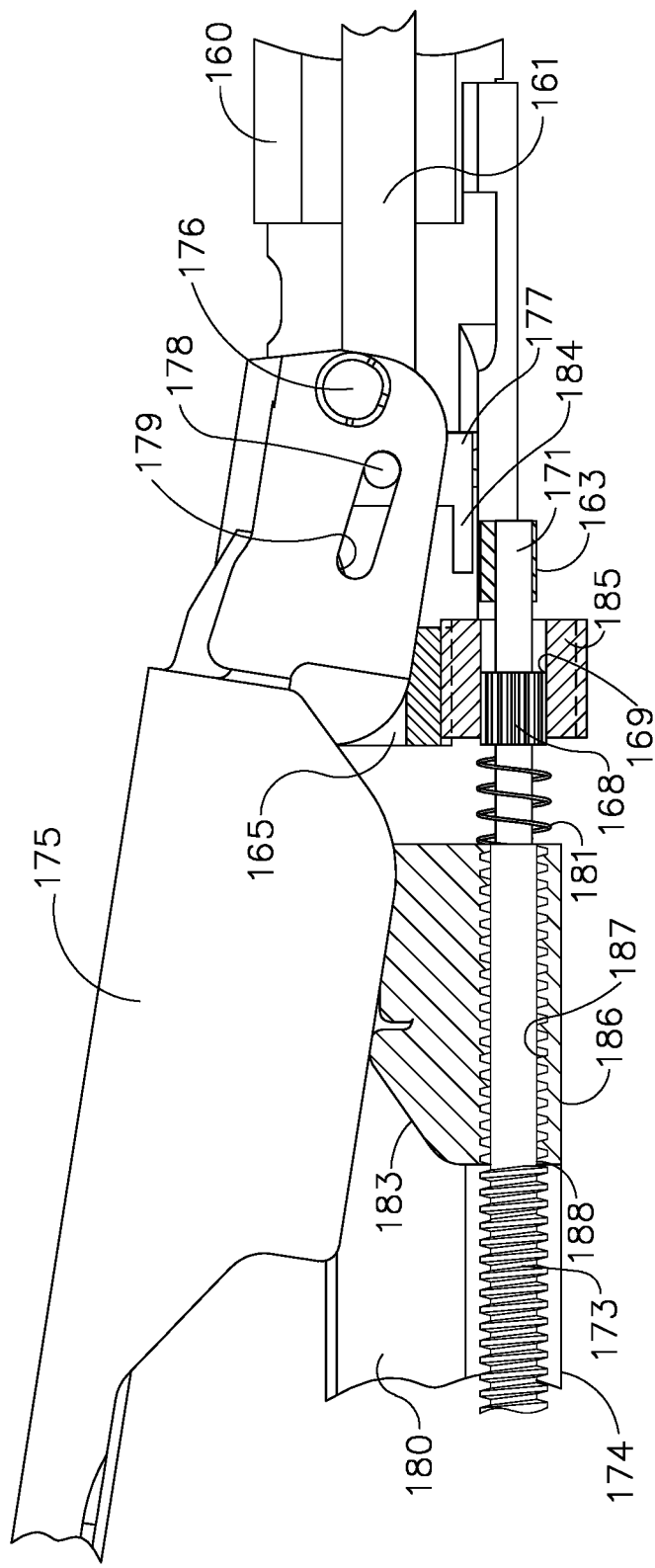
FIG. 8 is a partial cross-sectional elevational view of the end effector of FIG. 6 illustrating the end effector in an open, unfired configuration.

Referring primarily to FIGS. 7-9, the shaft 160 includes a rotatable input shaft 161. As described in greater detail further below, the input shaft 161 is utilized to operate the closing drive and the firing drive. The input shaft 161 is rotatably mounted in the shaft 160 by one or more bearings and comprises a threaded portion 172. The closure drive comprises a closure nut 177 which includes a threaded aperture 162 defined therein. The closure nut 177 further comprises closure pins 178 extending from opposite sides thereof which are slidably positioned in closure slots 179 defined in opposite sides of the anvil portion 175.

The threaded aperture 162 of the closure nut 177 is threadably engaged with the threaded portion 172 of the input shaft 161 such that, when the input shaft 161 is rotated in a first direction, the closure nut 177 is displaced distally toward the end of the end effector 170 and, when the input shaft 161 is rotated in a second, or opposite, direction, the closure nut 177 is displaced proximally toward the housing 152, as illustrated in FIG. 10. The interaction between the closure pins 178 of the closure nut 177 and the sidewalls of the closure slots 179 prevent the closure nut 177 from rotating with the input shaft 161 and, as a result, the rotational motion of the input shaft 161 is converted to longitudinal translation of the closure nut 177.

Figure 13:
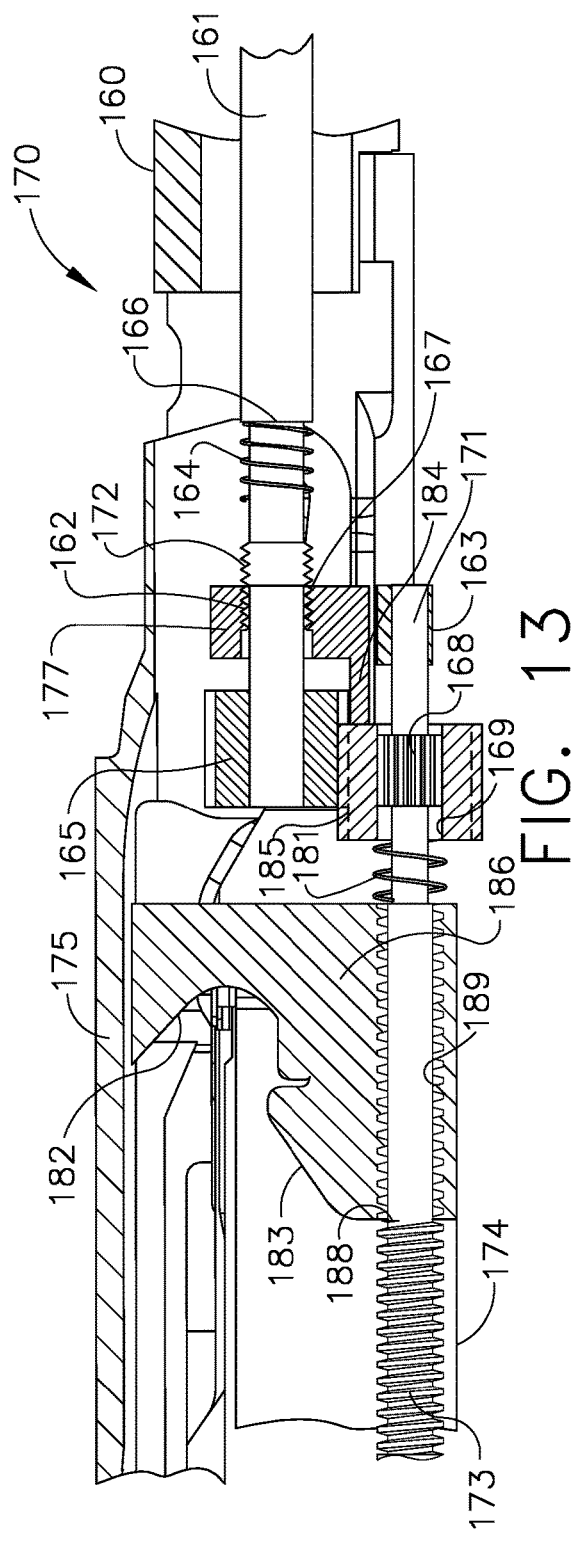
FIG. 13 is a partial cross-sectional elevational view of the end effector of FIG. 6 illustrating the closure system in a fully closed configuration and the firing system in a fully retracted configuration.
Figure 14:
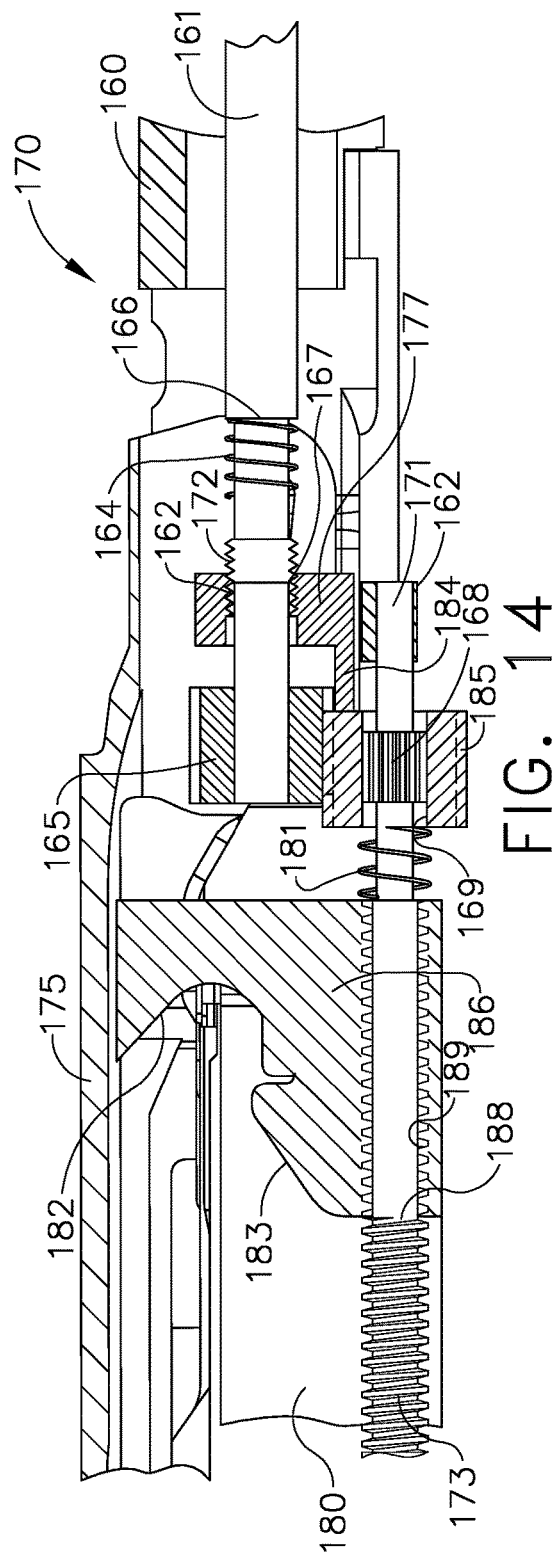
FIG. 14 is a partial cross-sectional elevational view of the end effector of FIG. 6 illustrating the closure system in the process of being returned to an open configuration and the firing system in a fully retracted configuration.

In use, the closure nut 177 is advanced distally by the input shaft 161 to move the anvil portion 175 between an open position (FIGS. 6-9) and a closed position (FIGS. 11-13). In such instances, the closure pins 178 engage the bottom sidewalls of the closure slot 179 and cam the anvil 175 toward the staple cartridge 180, as illustrated in FIG. 10. Similarly, referring to FIG. 14, the closure nut 177 is advanced proximally by the input shaft 161 to move the anvil portion 175 between a closed position and an open position. In such instances, the closure pins 178 engage the top sidewalls of the closure slot 179 and cam the anvil 175 away from the staple cartridge 180.

The input shaft 161 further comprises a distal gear 165 fixedly mounted to the distal end thereof. When the input shaft 161 is rotated in the first direction, the distal gear 165 rotates in the first direction and, when the input shaft 161 is rotated in the second direction, the distal gear 165 rotates in the second direction. The firing drive of the end effector 170 comprises a rotatable firing shaft 171 which is rotatably mounted in the staple cartridge portion 174 by one or more bearings, such as bearing 163, for example. The firing shaft 171 comprises a proximal gear 185 and a threaded portion 173. The proximal gear 185 of the firing shaft 171 is meshingly engaged with the distal gear 165 of the input shaft 161 such that the input shaft 161 can drive the firing shaft 171 when the input shaft 161 is rotated. The proximal gear 185 is slidably mounted to the firing shaft 171. More specifically, the firing shaft 171 comprises a splined portion 168 and the proximal gear 185 includes a splined aperture 169 extending therethrough which is slidably coupled to the splined shaft portion 168. As a result, the proximal gear 185 can rotate the firing shaft 171 about a longitudinal axis and, in addition, slide longitudinally along the longitudinal axis, as described in greater detail below.

The firing drive further comprises a firing nut 186 which includes a threaded aperture 189 defined therein which is threadably engageable with the threaded portion 173 of the shaft 171. The firing nut 186 further comprises wedges 183 defined thereon which are configured to slide under the staple drivers 84 and lift the staples 81 toward the anvil portion 175 to staple tissue positioned between the staple cartridge 180 and the anvil portion 175. The firing nut 186 also comprises a cutting member 182 defined thereon which is configured to incise the stapled tissue. When the firing nut 186 is threadably engaged with the shaft 171 and the input shaft 161 is rotated in the first direction, the firing nut 186 is displaced distally toward the end of the end effector 170 to eject the staples 81 from the staple cartridge 180 and incise the tissue. When the firing nut 186 is threadably engaged with the threaded portion 173 of the shaft 171 and the input shaft 161 is rotated in the second direction, the firing nut 186 is displaced proximally toward the housing 152 to retract the wedges 183 and the cutting member 182 to their unfired position.

The above being understood, the surgical instrument system 150 comprises a system for switching between a clamping operating mode and a staple firing operating mode that is an improvement over the switching system disclosed in connection with the surgical instrument system of FIGS. 1-5. Referring again to FIGS. 7-9, the closure nut 177 is movable from a proximal position to a distal position during a clamping stroke in order to move the anvil portion 175 from its open position to its closed position. When the closure nut 177 is in its proximal position, the closure nut 177 is threadably engaged with the threads 172 defined on the input shaft 171. The closure system can comprise a biasing member, such as spring 164, for example, which is configured to bias the threads 162 of the closure nut 177 into engagement with, or maintain their engagement with, the threads 172 of the input shaft 171. The spring 164 is positioned intermediate the closure nut 177 and a shoulder 166 defined on the shaft 171.

As a result of the above, the initial rotation of the input shaft 161 in the first direction can immediately displace the closure nut 177 distally to begin closing the anvil portion 175. Moreover, if the input shaft 161 is inadvertently driven in the second direction when the closure nut 177 is in its proximal position, the closure nut 177 may move proximally and become disengaged from the threads 172 and enter into an idle condition. The spring 164, however, can maintain the threads 162 of the closure nut 177 in close proximity to the threads 172 of the input shaft 161 such that, when the input shaft 161 is rotated in the first direction, the threads 162 can catch the threads 172 and the closure nut 177 can be pulled distally to close the anvil portion 175.

Notably, further to the above, the rotation of the input shaft 161 being utilized to initiate the clamping stroke of the closure nut 177 is being transferred to the firing shaft 171 via the meshed gears 165 and 185. This rotation of the firing shaft 171 does not drive the firing nut 186 distally as the firing nut 186, at this point in the operation of the surgical instrument system 150, is not threadably engaged with the threads 173 of the firing shaft 171. Rather, the firing nut 185 is sitting in an idle position and the firing shaft 171 is rotating within the threaded aperture 169 defined in the firing nut 185. As discussed in greater detail below, the firing nut 185 is pushed onto the threads 173 by the closure nut 177 during a later portion of its clamping stroke.

Referring primarily now to FIG. 9, the closure nut 177 further comprises a distally-extending switch arm 184. When the closure nut 177 is in its proximal position, as illustrated in FIG. 9, the switch arm 184 is not in contact with the slidable proximal gear 185. During the distal movement of the closure nut 177, the switch arm 184 contacts the proximal gear 185, as illustrated in FIG. 10. As can be seen in FIG. 10, the anvil portion 175 has not yet reached its fully-closed position when the switch arm 184 initially makes contact with the proximal gear 185. Thus, the closure nut 177 engages the proximal gear 185 prior to completing its clamping stroke. As the closure nut 177 is moved further distally to complete its clamping stroke, the closure nut 177 displaces the proximal gear 185 distally along the splined portion 168 of the firing shaft 171. The distal displacement of the proximal gear 185 displaces a push spring 181, which is positioned intermediate the proximal gear 185 and the firing nut 186, distally. Moreover, the distal displacement of the push spring 181 displaces the firing nut 186 distally and into engagement with the threads 173. The threads 189 of the firing nut 186 comprise a distal-most thread 188 which can initiate the threaded engagement between the firing nut 186 and the firing shaft 171.

Upon comparing FIGS. 10 and 11, it can be appreciated that the spring 181 can become compressed when it is being utilized to push the firing nut 186 distally as described above. In such instances, the pushing force between the proximal gear 185 and the firing nut 186 can increase as the proximal gear 185 is moved distally toward the firing nut 186. In at least one instance, the displacement of the proximal gear 185 can be linearly proportional to the force that the spring 181 applies to the firing nut 186. The force applied to the firing nut 186 by the spring 181 can increase until the threads 189 of the firing nut 186 catch on the threads 173 and, as a result, the firing nut 186 is pushed distally by the firing shaft 171. Once the firing nut 186 is threadably engaged with the threads 173, the firing nut 186 can pull away from the spring 181, as illustrated in FIG. 12.

As a result of the above, the clamping operating mode can initiate the firing operating mode before the clamping operating mode has been completed. In at least one instance, it may be desirable to initiate the staple firing operating mode toward the end of the clamping operating mode such that the staples 81 are not fired until the anvil portion 175 has been at least suitably positioned. Moreover, the surgical instrument system 150 can comprise a sensor system, for example, configured to detect when the staple firing operating mode has been initiated, or is about to be initiated, and pause the electric motor which is driving the input shaft 161. Such a sensor system can be configured to detect the position of the closure nut 177, the firing nut 186, the proximal gear 185, and/or the spring 181, for example. In at least one such instance, the electric motor can be paused to allow the surgeon to assess whether they want to proceed with firing the staples into the tissue or re-open the anvil portion 175 to reposition the end effector 170. In at least one instance, the surgeon can be provided with two switches to selectively operate-a first button which will re-start the electric motor and proceed with the firing stroke or a second button which will reverse the electric motor to re-open the anvil portion 175, for example. The first button can be green, for example, and the second button can be red, for example. The first button can include indicia such as "GO FORWARD" thereon while the second button can have other indicia such as "GO BACK" thereon, for example. Such switches can be positioned on a remote control console and/or the handle of the surgical instrument, depending on the circumstances.

After the advancement of the closure nut 177 has initiated the firing operating mode by pushing the firing nut 186 onto the thread 173 of the firing shaft 171, as described above, the closure nut 177 will continue to move through its clamping stroke along the thread 172 of the input shaft 161 until the closure nut 177 runs off of the thread 172 and becomes operably disengaged from the input shaft 161. At such point, the anvil portion 175 will be in its fully closed position. Moreover, at such point, the closure nut 177 will be in an idle condition and the continued rotation of the input shaft 161 to operate the staple firing system will not advance the closure nut 177.

As described above, the firing nut 186 is advanced distally to eject the staples 81 from the staple cartridge 180. The firing nut 186 can be advanced to the distal end of the end effector 170 to complete a firing stroke, as illustrated in FIG. 12. The thread 173 on the firing shaft 171 can be configured such that the firing nut 186 remains threadably engaged with the firing shaft 171 when the firing nut 186 reaches the end of its firing stroke. In at least one such instance, the firing nut 186, the wedges 183, and/or the cutting member 182 can change the state of a switch 87 positioned at the distal end of the end effector 170 when the firing nut 186 reaches the end of its firing stroke. The switch 87 is in communication with the controller of the surgical instrument system 150 which can reverse the direction of the electric motor to rotate the input shaft 161 in its second direction when the state of the switch 87 is reversed. When the input shaft 161 is rotated in its second direction, the firing nut 186 is retracted toward its unfired position. In addition to or in lieu of the above, the surgical instrument 150 can include a switch which can be actuated by the surgeon to stop and/or reverse the direction of the electric motor.

Further to the above, referring now to FIG. 12, the firing nut 186 is retracted back to its unfired position to reset the firing system when the electric motor is operated in the second direction. As the firing nut 186 is being retracted, referring now to FIG. 13, the firing nut 186 comes into contact with the spring 181 and pushes the spring 181 proximally. The firing nut 186 contacts the spring 181 before the firing nut 186 runs off of, or disengages from, the thread 173. As the firing nut 186 pushes the spring 181 proximally, the spring 181 pushes the proximal gear 185 and the closure nut 177 proximally such that the closure nut 177 threadably re-engages the thread 172 of the input shaft 161, as illustrated in FIG. 13. The threaded aperture 162 of the closure nut 177 comprises a proximal thread 167 which catches the thread 172 to initiate the threaded engagement between the closure nut 177 and the input shaft 161. Once the closure nut 177 has been threadably re-engaged with the thread 172, the continued rotation of the input shaft 161 in the second direction moves the closure nut 177 proximally in order to cam the anvil portion 175 back into its open position and, as a result, reset the clamping system. Concurrently, the continued rotation of the input shaft 161 in the second direction can cause the firing nut 186 to be run off of, or become disengaged from, the threads 173 of the firing shaft 171. Once the firing nut 186 has become operably disengaged from the firing shaft 171, the firing system has been reset.

In use, the anvil portion 175 can be rotated away from its fully clamped position to release the tissue captured between the anvil portion 175 and the staple cartridge 180. Moreover, the anvil portion 175 may be moved between its open position and its closed position to clamp and release tissue, as needed, and/or to position the anvil portion 175 relative to the staple cartridge 180 such that the end effector 170 can be inserted into a patient through a trocar, for example. The pause feature described above can allow the surgical instrument system 150 to be operated in a first operating range to open and close the anvil portion 175 without firing the staples in the staple cartridge 180 and/or incising the tissue.

In addition to the aspects of the surgical instrument system of FIGS. 1-5 discussed above, the closure nut 77 engages the anvil portion 75 at the proximal end thereof and, as a result, the closure nut 77 may not be able to push the distal end of the anvil portion 75 into its fully-closed position; moreover, the firing nut 86 does not include a camming member which can pull the distal end of the anvil portion 75 into its fully-closed position. As such, the tissue gap between the distal ends of the anvil portion 75 and the staple cartridge 80 may be larger than the tissue gap between the proximal ends of the anvil portion 75 and the staple cartridge 80 which can result in the distal staples not being formed to the correct, or an at least suitable, formed height. Improvements to this arrangement are discussed further below.

Figure 15:
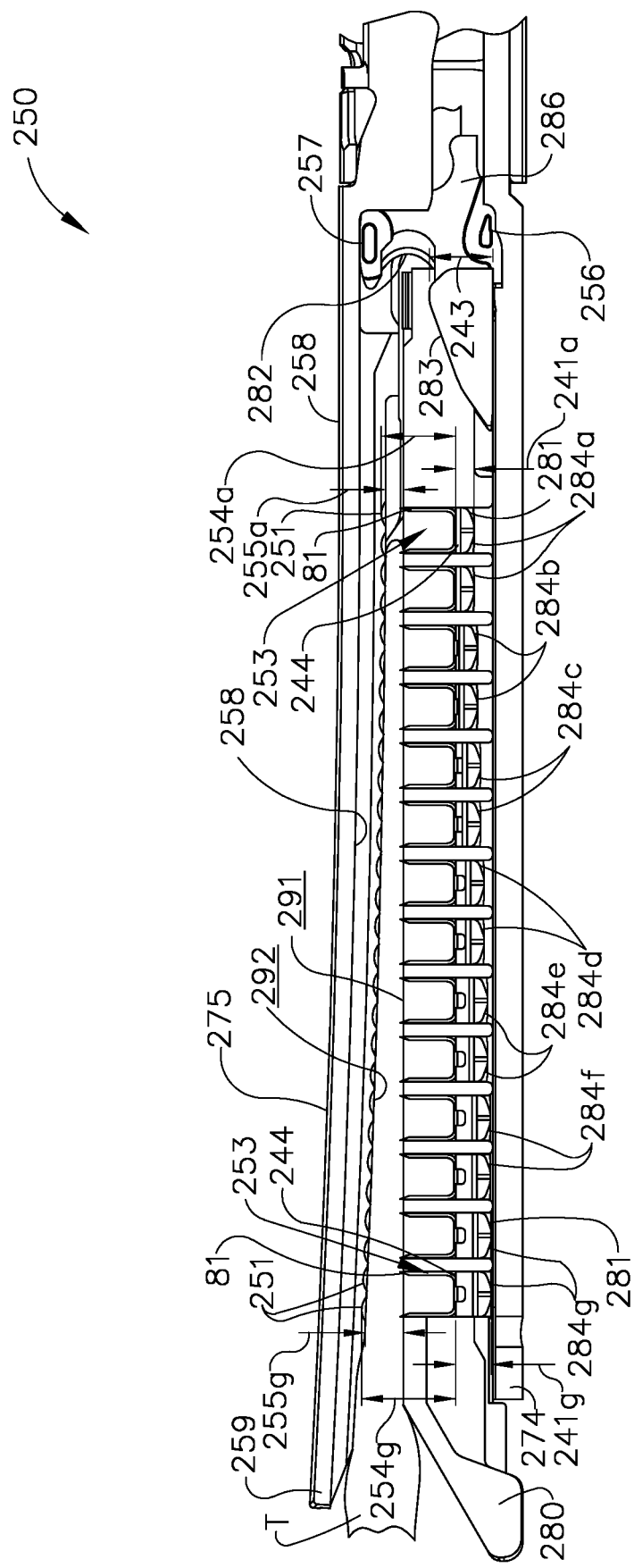
FIG. 15 is a partial cross-sectional elevational view of an end effector comprising a staple firing system configured to compensate for an uneven gap between an anvil and a staple cartridge of the end effector in accordance with at least one embodiment.

An end effector 270 of a surgical instrument system 250 is illustrated in FIG. 15. The end effector 270 comprises a staple cartridge portion 274 and an anvil portion 275. The end effector 270 further comprises a staple cartridge 280 positioned in the staple cartridge portion 274. Similar to the above, the staple cartridge 280 is readily removable from the staple cartridge portion 274 and readily replaceable with another staple cartridge. Other embodiments are envisioned in which the staple cartridge 280 is not readily removable from the staple cartridge portion 274. The anvil portion 275 is rotatable relative to the staple cartridge 280 between an open position and a closed position to compress tissue T therebetween. Other embodiments are envisioned in which the staple cartridge portion 274 is rotatable relative to the anvil portion 275. In either event, the end effector 270 is movable between an open configuration and a closed configuration in any suitable manner. In at least one instance, the end effector 270 is moved from its open configuration to its closed configuration by cams 256 and 257 extending from the firing nut 286. More specifically, the cam 257 is configured to enter a longitudinal cam slot 258 defined in the anvil portion 275 and the cam 256 is configured to engage the staple cartridge portion 274 and/or the staple cartridge 280 and co-operatively position the anvil portion 275 relative to the staple cartridge 280 when the firing nut 286 is advanced distally. In other embodiments, the firing nut 286 does not comprise cams to move the end effector 270 between its open configuration and its closed configuration. In at least one such instance, the end effector comprises a closing system which is separate and distinct from the staple firing system of the end effector. The examples provided herein are adaptable to both embodiments.

The staple cartridge 280 comprises a deck 291 configured to support tissue thereon and a plurality of staple cavities 253 defined in the deck 291. Staples 81, for example, are removably stored in the staple cavities 253. Each staple 81 comprises the same configuration. For instance, each staple 81 can comprise a U-shaped configuration or, alternatively, a V-shaped configuration, for example. A staple having a U-shaped configuration comprises a base and two legs extending from the base which extend in parallel directions to one another. A staple having a V-shaped configuration comprises a base and two legs extending from the base which extend in non-parallel directions to one another. Each staple 81 stored in the staple cartridge 280 is defined by the same unformed height. The unformed height of a staple 81 is the overall height of the staple measured from a plane including the bottom surface of its base to a plane including the tips of its legs. The staples 81 can have an unformed height of 2.0 mm, 2.5 mm, 3.0 mm, 3.5 mm, or 4.0 mm, for example. The staple cartridge 280 further comprises a plurality of staple drivers 284a-284g positioned in the staple cavities 253 which support the staples 81 in the staple cavities 253. The firing nut 286 comprises wedge surfaces 283 defined thereon which are configured to slide underneath the staple drivers 284a-284g and sequentially lift the staple drivers 284a-284g, and the staples 81 supported thereon, toward the anvil portion 275. Each staple driver 284a-284g comprises a ramp surface 281 defined on the bottom surface thereof which is engaged by the wedge surfaces 283 as the firing nut 286 is advanced distally. The anvil portion 275 comprises a plurality of staple forming pockets 251 defined therein which are configured to deform the staples 81 as they are ejected from the staple cavities 253.

Further to the above, the anvil portion 275 further comprises a tissue compression surface 292 defined thereon which is configured to compress tissue against the cartridge deck 291 when the anvil portion 275 is moved into its fully closed position. When the anvil portion 275 is in its fully closed position, it may be desirable for the anvil compression surface 292 to be parallel to the cartridge deck 291. In such a position, the gap, i.e., tissue gap, between the anvil compression surface 292 and the cartridge deck 291 is constant along the longitudinal length of the end effector 270. Stated another way, the tissue gap over the proximal-most staple cavity, i.e., tissue gap 255a, is the same as the tissue gap over the distal-most staple cavity, i.e., tissue gap 255g, when the anvil portion 275 is parallel to the staple cartridge 280. Such a parallel position of the anvil portion 275, however, may not always be achievable in some instances. In certain instances, the tissue T positioned between the anvil compression surface 292 and the cartridge deck 291 may be thick and the anvil portion 275 may not reach a parallel position when the anvil portion 275 reaches its final, or fully-clamped, position. Moreover, in some instances, the distal end 259 of the anvil portion 275 may deflect or bend upwardly when the end effector 270 is clamped onto thick tissue, for example. In either event, as illustrated in FIG. 15, the distal end 259 of the anvil portion 275 can be positioned further away from the cartridge deck 291 than the proximal end 258. In such instances, as a result, the tissue gap over the distal-most staple cavity, i.e., tissue gap 255g, is larger than the tissue gap over the proximal-most staple cavity, i.e., tissue gap 255a.

The firing nut 286 comprises a cutting surface, such as knife 282, for example, configured to transect the tissue positioned intermediate the tissue compression surface 292 and the cartridge deck 291 as the firing nut 286 is advanced distally to drive the staples 81 toward the anvil portion 275, as described above.

Further to the above, each staple 81 is formed within a forming gap. The forming gap for a staple 81 is the distance between a support surface on the staple driver supporting the staple 81, such as support surfaces 244 on staple drivers 284a-284g, for example, and the corresponding forming pocket 251 defined in the anvil portion 254 when the staple driver has reached its fully-fired position. The staple driver reaches its fully-fired position when the crest, or apex, of the wedges 283 passes under the bottom surface of the staple driver. The apex of the wedges 283 is defined by an apex height 243. As the firing nut 286 is advanced distally, the crest of the wedges 283 sequentially passes under the staple drivers 284a-284g to sequentially eject and deform the staples 81. During the initial portion of the firing nut 286 progression, the wedges 283 lift the drivers 284a toward the anvil portion 275. As the wedges 283 are moving the drivers 284a to their fully-fired positions, the wedges 283 begin to lift the drivers 284b toward the anvil portion 275. As the wedges 283 are moving the drivers 284b to their fully-fired positions, the wedges 283 begin to lift the drivers 284c toward the anvil portion 275, and so forth. In alternative embodiments, the wedges 283 may not begin to lift the drivers 284b until after the drivers 284a have been lifted to their fully-fired positions and, similarly, may not begin to lift the drivers 284c until after the drivers 284b have been lifted to their fully-fired positions, and so forth.

As discussed above, the forming gap for a staple 81 is defined between the support surface 244 of the driver supporting the staple 81 and the forming pocket 251 positioned opposite the staple 81 when driver has reached its fully-fired position. Referring to FIG. 15, a forming gap distance 254a is defined between the support surface 244 of the staple drivers 284a and the forming pockets 251 positioned opposite the staple drivers 284a. Similarly, a forming gap distance 254g is defined between the support surface 244 of the staple drivers 284g and the forming pockets 251 positioned opposite the staple drivers 284g. The reader should note, however, that the forming gap distances 254a and 254g depicted in FIG. 15 do not represent the fully-fired positions of the staple drivers 284a and 284g. In fact, the staple drivers 284a and 284g are illustrated in unfired positions in FIG. 15. Thus, it should be appreciated that the distances 254a and 254g will shorten as the staple drivers 284a and 284g are lifted toward the anvil portion 275.

As discussed above, the orientation of the anvil portion 275 can affect the tissue gap between the staple cartridge 280 and anvil portion 275. The orientation of the anvil portion 275 can also affect the forming gaps for the staples 81 within the end effector 270. When the distal end 259 of the anvil portion 275 is positioned further away from the staple cartridge 280 than the proximal end 258, as illustrated in FIG. 15, the forming gaps for the staples 81 at the distal end of the end effector 270 may be larger than the forming gaps for the staples 81 at the proximal end of the end effector 270, absent some compensatory measure. If such a compensatory measure is not undertaken, the distal staples 81 will be formed to a different height than the proximal staples 81. In at least one such instance, the staples 81 may be formed within a height range including the tallest formed staple at the distal end of the end effector 270 and the shortest formed staple at the proximal end of the end effector 270. In some instances, such a formed height range of the staples 81 can be suitable, especially if the gradient amongst the formed staple heights is small. In other instances, the proximal staples 81 may be deformed to a suitable height while the distal staples 81 may not be deformed to a suitable height.

The end effector 270 is configured to compensate for instances where the anvil portion 275 is not parallel to the staple cartridge 280. Stated another way, the end effector 270 is configured such that there is little, if any, difference in the forming gaps for the staples 81 when the anvil portion 275 has not been closed to a parallel position relative to the deck 291 of the staple cartridge 280. To achieve this result, the support surfaces 244 of the staple drivers 284a-284g can be lifted to different heights in a manner which corresponds to the orientation of the anvil portion 275. For instance, the support surfaces 244 of the staple drivers 284a are lifted to a first height relative to the cartridge deck 291 and the support surfaces 244 of the staple drivers 284b are lifted to a second height relative to the cartridge deck 291 which is greater than the first height. Similarly, the support surfaces 244 of the staple drivers 284c are lifted to a third height relative to the cartridge deck 291 which is greater than the second height. The arrangement of the first height, the second height, and the third height is consistent with an angled anvil portion 275. This arrangement further includes the support surfaces 244 of the staple drivers 248d which are lifted to a fourth height that is greater than the third height, the support surfaces 244 of the staple drivers 248e which are lifted to a fifth height that is greater than the fourth height, the support surfaces 244 of the staple drivers 248f which are lifted to a sixth height that is greater than the fifth height, and the support surfaces 244 of the staple drivers 248g which are lifted to a seventh height that is greater than the sixth height, for example. The support surfaces 244 extend above the cartridge deck 291 when the staple drivers 284a-284g are in their fully-fired positions; however, alternative embodiments are envisioned where some of the support surfaces 244 or all of the support surfaces 244 may not extend above the deck 291.

As discussed above, the staple drivers 284a-284g are lifted to different heights. The first lift height of the support surfaces 244 is equal to the sum of the apex height 243 of the wedges 283 and the driver height 241a of the staple drivers 284a. Similarly, the second lift height of the support surfaces 244 is equal to the sum of the apex height 243 of the wedges 283 and the driver height 241b of the staple drivers 284b. While the apex height 243 of the wedges 283 is the same for the first lift height and the second lift height, the driver height 241a is shorter than the driver height 241b and, as a result, the first lift height is shorter than the second lift height. Similarly, the third lift height of the support surfaces 244 is equal to the sum of the apex height 243 of the wedges 283 and the driver height 241c of the staple drivers 284c, which is taller than the driver height 241b of the staple drivers 284b. Along these lines, the driver height 241d of the staple drivers 284d is taller than the driver height 241c of the staple drivers 284c, the driver height 241e of the staple drivers 284e is taller than the driver height 241d of the staple drivers 284*d*, the driver height 241*f* of the staple drivers 284*f* is taller than the driver height 241*e* of the staple drivers 284*e*, and the driver height 241*g* of the staple drivers 284*g* is taller than the driver height 241*f* of the staple drivers 284*f*.

Each of the staple support surfaces 244 comprises a trough, or groove, defined in the top of a driver 284*a*-284*g*. Each trough is configured to receive the base of a staple 81. The troughs are configured to closely receive the bases of the staples 81 such that there is little, if any, relative lateral movement between the staple bases and the support surfaces 244. Further to the above, the forming distances for the staples 81 is measured from the bottom of the troughs to the top of the corresponding forming pockets 251 defined in the anvil portion 275. Each trough comprises a substantially U-shaped, or rounded bottom, configuration; however, any suitable configuration can be used, such as a V-shaped, or angled bottom, for example. In either event, each trough can comprise a cradle for supporting a staple 81.

As discussed above, the staple support surfaces 244 of the staple drivers 284*a*-284*g* are lifted to different heights in order to eliminate, or at least mitigate, differences in the forming gaps for the staples 81 between the staple support surfaces 244 and the anvil forming pockets 251. In certain embodiments, it is desirable for all of the staples of the staple cartridge 280 to be formed to the same, or at least substantially the same, formed height. In other embodiments, it is desirable to form all of the staples in a first longitudinal row to a first formed height and all of the staples in a second longitudinal row to a second formed height which is different than the first formed height. The examples provided above can be adapted to such embodiments. For instance, a first set of staple drivers having a first range of driver heights can be used to deploy a first longitudinal row of staples and a second set of staple drivers having a second range of driver heights can be used to deploy a second longitudinal row of staples wherein the second range of driver heights is different than the first range of driver heights. In at least one such instance, the second range of driver heights can be taller than the first range of driver heights. In certain embodiments, the first set of staple drivers are not connected to the second set of staple drivers; however, embodiments are envisioned in which a driver from the first set of staple drivers is connected to a driver from the second set of staple drivers. In at least one instance, two or more drivers within the same longitudinal row can be connected to each other.

Further to the above, embodiments are envisioned which comprise three or more longitudinal rows of staples which are formed to different formed heights utilizing different forming gaps. In at least one embodiment, the forming gap for the first row of staples is at least partially determined by a first wedge 283, the forming gap for the second row of staples is at least partially determined by a second wedge 283, and the forming gap for the third row of staples is at least partially determined by a third wedge 283. In such an embodiment, the apex height 243 of the first wedge 283 is different than the apex height 243 of the second wedge 283. Similarly, the apex height 243 of the third wedge 283 is different than the apex height 243 of the first wedge 283 and the second wedge 283.

In various instances, the staples in a first longitudinal row of staples can have a first undeformed height and the staples in a second longitudinal row of staples can have a second undeformed height which is different than the first undeformed height. Similarly, the staples in a third longitudinal row of staples can have a third undeformed height which is different that the second undeformed height.

As illustrated in FIG. 15, the staple cartridge 280 comprises two staple drivers 284*a*, two staple drivers 284*b* positioned distally with respect to the staple drivers 284*a*, two staple drivers 284*c* positioned distally with respect to the staple drivers 284*b*, two staple drivers 284*d* positioned distally with respect to the staple drivers 284*c*, two staple drivers 284*e* positioned distally with respect to the staple drivers 284*d*, two staple drivers 284*f* positioned distally with respect to the staple drivers 284*e*, and two staple drivers 284*g* positioned distally with respect to the staple drivers 284*f* which are arranged in a single longitudinal row. Other embodiments are envisioned in which the staple cartridge 280 does not comprise staple drivers having the same driver height within the same longitudinal row. In at least one such embodiment, each staple driver within a longitudinal row has a different driver height. Various other embodiments are envisioned which comprise any suitable arrangement of staple drivers in any suitable pattern.

The driver heights of the drivers 284*a*-284*g* have a linear gradient. The drivers 284*g* are taller by a height X than the drivers 284*f*, the drivers 284*f* are taller by the height X than the drivers 284*e*, the drivers 284*e* are taller by the height X than the drivers 284*d*, and so forth. In various alternative embodiments, the driver heights of the drivers 284*a*-284*g* can have any other suitable gradient, such as a geometric gradient, for example.

As described above, the drivers 284*a*-284*g* are illustrated in their unfired, or unlifted, positions in FIG. 15. As also illustrated in FIG. 15, the drivers 284*a*-284*g* are supported in their unfired positions within the staple cartridge 280 such that the tips of the staples 81 are positioned flush with, or at least nearly flush with, the cartridge deck 291. In such instances, the tips of the staples 81 may be positioned flush with the cartridge deck 291, positioned slightly below the cartridge deck 291, and/or positioned slightly above the cartridge deck 291 when the staple drivers 284*a*-284*g* are in their unfired positions. In alternative embodiments, a significant portion of the staples 81 can extend above the cartridge deck 291 when the staple drivers 284*a*-284*g* are in their unfired positions. In at least one such embodiment, an adjunct material can be positioned over the cartridge deck 291 and the tips of the staples 81 can be embedded in the adjunct material prior to the staples 81 being lifted by the staple drivers 284*a*-284*g*. Various adjunct materials can include a tissue thickness compensator, a buttress material, and/or any suitable layer, for example. The entire disclosure of U.S. Pat. No. 8,393,514, entitled SELECTIVELY ORIENTABLE IMPLANTABLE FASTENER CARTRIDGE, which issued on Mar. 12, 2013, is incorporated by reference herein.

In certain alternative embodiments, although not illustrated, some of the staples 81 may extend above the cartridge deck 291 while some of the staples 81 may not extend above the cartridge deck 291 when the staple drivers 284*a*-284*g* are in their unfired positions. In at least one such embodiment, the proximal staples 81 are positioned below the cartridge deck 291 while the distal staples 81 are positioned above the cartridge deck 291 when the staple drivers 284*a*-284*g* are in their unfired positions. The staple drivers 284*a*-284*g* can be positioned and arranged such that there is a height gradient between the initial, or unfired, position of the proximal-most staple 81 and the initial, or unfired, position of the distal-most staple 81 of a longitudinal row of staples when the staple drivers 284*a*-284*g* are in their unfired positions. This gradient is a linear gradient; however, alternative embodiments are envisioned in which the gradient comprises a geometric gradient, for example.

Further to the above, alternative embodiments are envisioned in which the staple drivers 284a-284g are stored within the staple cartridge 280 such that the bottom drive surfaces thereof are aligned with one another when the staple drivers 284a-284g are in their unfired, or unlifted, positions. In such instances, the staples 81 are supported at different distances relative to the cartridge deck 291. Such initial positioning of the staple drivers 284a-284g does not affect the forming gaps for the staples 81 discussed above as the forming gaps are set by the final position of the staple drivers 284a-284g.

Further to the above, the cartridge deck 291 of the staple cartridge 280 comprises a flat, or an at least substantially flat, surface; however, alternative embodiments are envisioned in which the cartridge deck 291 is not flat. In at least one embodiment, the distal end of the cartridge deck 291 is taller than the proximal end of the cartridge deck 291. In at least one such embodiment, the cartridge deck 291 slopes linearly between the proximal end and the distal end. In other embodiments, the cartridge deck 291 slopes geometrically between the proximal end and the distal end. In various embodiments, the cartridge deck 291 comprises longitudinal steps having different heights. For instance, the cartridge deck 291 can comprise a first longitudinal step which is aligned with a first longitudinal row of staple cavities, a second longitudinal step which is aligned with a second longitudinal row of staple cavities, and a third longitudinal step which is aligned with a third longitudinal row of staple cavities, for example. The transition between adjacent longitudinal steps can be a vertical wall or a sloped, or angled, wall, for example.

As discussed above, the staples 81 in the staple cartridge 280 have the same, or at least substantially the same, unformed height. As also discussed above, the unformed height of the staples in a first row can be different than the unformed height of the staples in a second row. In certain embodiments, the staples within a longitudinal row can have different unformed heights. In at least one such embodiment, the proximal-most staple in the row can have a first unformed height and the distal-most staple in the row can have a second unformed height. In such an embodiment, the staples between the proximal-most staple and the distal-most staple can progressively increase in height. The staples can increase in height between the proximal end and the distal end of the end effector according to a gradient. In at least one instance, the gradient is a linear gradient, for example. In certain instances, the gradient is a geometric gradient, for example.

Embodiments comprising staples having different unformed heights within a row of staples can be used in conjunction with staple drivers having different driver heights. In at least one embodiment, the proximal-most staple in a row can be the shortest staple in the row and can be driven by the shortest staple driver, for example. Moreover, in such an embodiment, the distal-most staple can be the tallest staple in the row and can be driven by the tallest staple driver, for example. In at least one embodiment, the shortest staples in a row are paired with the shortest staple drivers and the tallest staples in a row are paired with the tallest staple drivers, and so forth. In certain other embodiments, the shortest staples in a row are not paired with the shortest staple drivers and the tallest staples are not paired with the tallest staple drivers. For instance, the shortest staples can be driven by the tallest staple drivers and the tallest staples can be driven by the shortest staple drivers, for example. In the end, the staples and the staple drivers can be paired in any suitable manner to properly fasten the tissue.

As discussed above, the staples 81 in the staple cartridge 280 have the same, or at least substantially the same, configuration, i.e., a V-shaped configuration, for example. Alternative embodiments are envisioned in which the staples in a row of staples have different configurations. In at least one embodiment, each of the staples in a row of staples can have a V-shaped configuration but the angle of the staple legs that forms the V-shaped configuration can be different for at least some of, if not all of, the staples. For instance, the proximal-most staple in a row of staples can have a narrow V-shaped configuration and the distal-most staple in the row of staples can have a wide V-shaped configuration, for example. In at least one such instance, the angle of the staple legs can increase proximally to distally. In other instances, the angle of the staple legs can decrease proximally to distally. In either event, the angle of the staple legs can affect the formed height of the staples and can be selectively used to secure the tissue in a desired manner.

Another unformed configuration of a staple can include a W-shaped staple, for example. A W-shaped staple can comprise a V-shaped staple with a portion of the staple base extending upwardly to create a substantially W-shaped configuration. W-shaped staples are sometimes referred to as M-shaped or gull-winged staples. The entire disclosure of U.S. Pat. No. 5,725,554, entitled SURGICAL STAPLE AND STAPLER, which issued on Mar. 10, 1998, is incorporated by reference herein. In at least one embodiment, a longitudinal row of staples can include V-shaped staples at the proximal end of the staple row and W-shaped staples at the distal end of the staple row, for example. The W-shaped staples can form differently than the V-shaped staples and may be more suitable for stapling tissue in larger forming gaps, for example.

A surgical instrument system 350 is illustrated in FIGS. 16-20. The surgical instrument system 350 includes a shaft assembly 360 and an end effector 370 extending from the shaft assembly 360. In this embodiment, as well as others, the shaft assembly 360 extends from a housing of the type described above which is configured to be attached to a robotic surgical system, such as the DAVINCI robotic surgical system manufactured by Intuitive Surgical, Inc., for example. Alternatively, the shaft assembly 360 can extend from a handle of a surgical instrument configured to be grasped and operated by a surgeon, for example. Such hand-held surgical instruments may employ one or more electric motors to generate the closure and firing motions or the closure and firing motions may be manually generated by manipulating one or more triggers or actuation arrangements supported on the handle or housing. All of such variations may be effectively employed with the surgical instrument system 350 and may be encompassed by the Claims appended hereto. Further details of such handles, housings and shaft assemblies are found in the various disclosures that have been herein incorporated by reference. Similar to the above-described arrangements, the shaft assembly 360 may also comprise at least one articulation joint, such as articulation joint 364, for example, which is configured to permit the end effector 370 to be articulated about at least one axis of rotation. Other embodiments are envisioned in which the shaft assembly 360 does not comprise an articulation joint.

Figure 16:
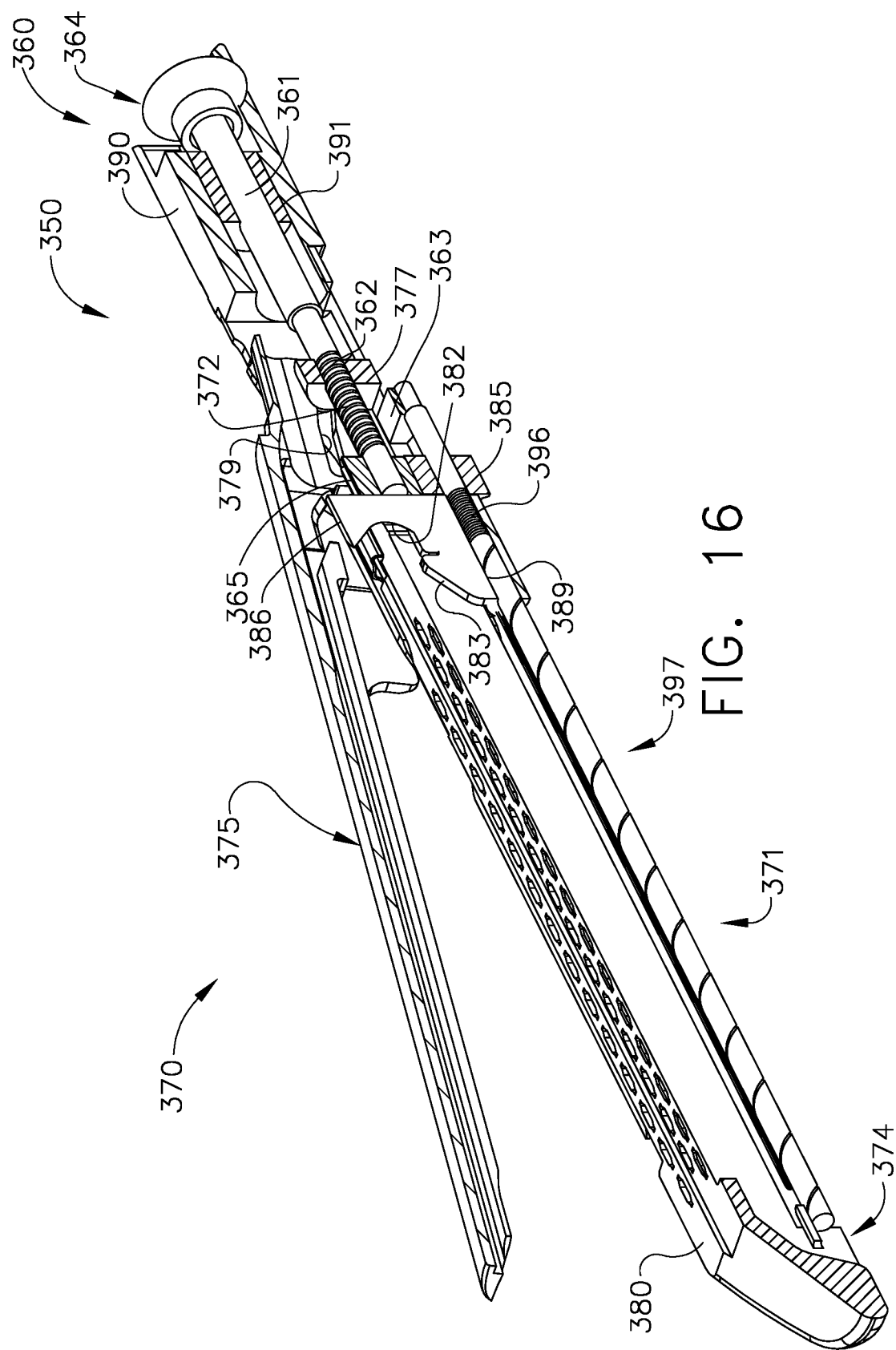
FIG. 16 is a longitudinal cross-sectional view of an end effector of a surgical instrument system illustrated in an open, or unclamped configuration which includes a staple cartridge, staples removably stored in the staple cartridge, and an anvil configured to deform the staples.

Referring primarily to FIG. 16, the end effector 370 comprises a staple cartridge portion 374 and an anvil portion 375. A staple cartridge 380 is positioned in the staple cartridge portion 374. The staple cartridge 380 is removable from the staple cartridge portion 374 such that it can be readily replaced with another staple cartridge; however, other embodiments are envisioned in which the staple cartridge 380 is not readily replaceable. The anvil portion 375 is movable relative to the staple cartridge portion 374 about anvil trunnions or pivot pins 376 extending from the anvil portion 375. See FIGS. 18, 20 and 22. For example, an anvil trunnion 376 extends laterally from each lateral side of the anvil portion 375 to be movably received within a corresponding opening or slot (not shown) that is formed in the staple cartridge portion 374. Alternative embodiments are envisioned in which the staple cartridge portion 374 is "rotatable", "movable" or "pivotable" relative to the anvil portion 375. The anvil portion 375 is movable between an open position (FIGS. 16-18) and a fully-closed position (FIGS. 19-22) by a closure drive as described in greater detail further below. Staples, such as staples 381, for example, are removably stored in the staple cartridge 380 and can be ejected from the staple cartridge 380 by a firing drive and deformed against the anvil portion 375, as also described in greater detail below.

Referring primarily to FIGS. 16-18, the shaft assembly 360 includes a rotatable input shaft 361. As described in greater detail further below, the input shaft 361 is utilized to operate the closing drive and the firing drive. The input shaft 361 is rotatably mounted in a "ground" or "spine" portion 390 of the shaft assembly 360 by one or more bearings 391 and comprises a threaded portion 372. See FIG. 16. The closure drive comprises a closure nut 377 which includes a threaded aperture 362 defined therein. The closure nut 377 further comprises closure pins 378 extending from opposite sides thereof which are slidably positioned in closure slots 379 defined in opposite sides of the anvil portion 375.

The threaded aperture 362 of the closure nut 377 is threadably engaged with the threaded portion 372 of the input shaft 361 such that, when the input shaft 361 is rotated in a first direction, the closure nut 377 is displaced distally toward the end of the end effector 370 in a distal direction "DD" and, when the input shaft 361 is rotated in a second, or opposite, direction, the closure nut 377 is displaced proximally toward the housing in a proximal direction "PD", as illustrated in FIGS. 16-18. The interaction between the closure pins 378 of the closure nut 377 and the sidewalls of the closure slots 379 prevent the closure nut 377 from rotating with the input shaft 361 and, as a result, the rotational motion of the input shaft 361 is converted to longitudinal translation of the closure nut 377.

In use, the closure nut 377 is advanced distally by the input shaft 361 to move the anvil portion 375 between an open position (FIGS. 16-18) and fully-closed positions (FIGS. 19-22). In such instances, the closure pins 378 engage the bottom sidewalls of each closure slot 379 and cam the anvil portion 375 toward the staple cartridge 380. Referring primarily to FIGS. 19 and 20, it can be observed that in at least the illustrated embodiment, the closure slots 379 have a somewhat arcuate shape. Stated another way, for example, each of the closure slots 379 has a proximal slot portion 392 and a distal slot portion 394. The point or location where the proximal slot portion 392 transitions to the distal slot portion 394 is referred to herein and the apex 395. See FIGS. 20 and 22. When the closure nut 377 is in the proximal-most position (e.g., the "beginning position"- FIGS. 16-18), the anvil portion 375 is held in the open position. When the closure nut 377 is in that beginning position, the closure pins 378 are at the proximal end of the proximal slot portions 392 of each closure slot 379. The mechanical advantage attained between the closure pins 378 and the closure slots 379 and by virtue of the engagement of the anvil trunnions 376 with the cartridge portion 374 will serve to retain the anvil portion 375 in the open orientation. When the surgeon desires to close the anvil portion 375, the input shaft 361 is rotated in a first direction to drive the closure nut 377 distally. As the closure pins 378 advance distally through the proximal slot portions 392, the anvil portion 375 starts camming closed. Once the closure pins 378 reach the apex 395, the anvil portion 375 is retained in the "fully closed" or "fully clamped" position. Continued rotation of the input shaft 361 will result in the continued distal advancement of the closure nut 377. As the closure nut 377 continues to move distally, the closure pins 378 continue to advance distally within the distal slot portions 394 all the while maintaining the camming or closure force on the anvil portion 375 to positively retain it in the closed position. When the surgeon desires to return the anvil portion 375 to the open position, the input shaft 361 is rotated in the opposite or second direction which drives the closure nut 377 proximally back to its proximal-most or beginning position. Because the closure nut 377 is positively engaged with the input shaft 361 or, stated another way, because the closure nut 377 is threadably engaged with the threads 372 on the input shaft 361, a positive closure force is maintained on the anvil portion 375 throughout the closure and firing processes. Such arrangement may therefore avoid anvil movement or chatter that may be encountered by prior arrangements wherein the closure nut is loosely journaled on a portion of the input shaft during the firing process.

The input shaft 361 further comprises a distal gear 365 fixedly mounted to the distal end thereof. When the input shaft 361 is rotated in the first direction, the distal gear 365 rotates in the first direction and, when the input shaft 361 is rotated in the second direction, the distal gear 365 rotates in the second direction. The firing drive of the end effector 370 comprises a rotatable firing shaft 371 which is rotatably mounted in the staple cartridge portion 374 by one or more bearings, such as bearing 363, for example. The firing shaft 371 comprises a proximal gear 385, a proximal threaded portion 396 and a distal threaded portion 397. In the illustrated embodiment, the proximal thread portion 396 has a first thread "lead" that differs from the second thread lead of the distal thread portion 397 as will be discussed in further detail below. The proximal gear 385 of the firing shaft 371 is meshingly engaged with the distal gear 365 of the input shaft 361 such that the input shaft 361 can drive the firing shaft 371 when the input shaft 361 is rotated. The proximal gear 385 is keyed onto the firing shaft 371 such that rotation of the proximal gear 385 results in rotation of the firing shaft 371.

The firing drive further comprises a firing nut 386 which includes an axial aperture 389 and a drive member 398. In the illustrated embodiment, the drive member 398 is received within an aperture 399 in the firing nut 386 and may be biased into driving engagement with the thread portions on the firing shaft 371 by a biasing member or spring (not shown). The firing nut 386 further comprises wedges 383 defined thereon which are configured to slide under the staple drivers and lift the staples 381 toward the anvil portion 375 to staple tissue positioned between the staple cartridge 380 and the anvil portion 375. The firing nut 386 also comprises a cutting member 382 defined thereon which is configured to incise the stapled tissue. When the firing nut 386 is threadably engaged with the distal thread portion 397 of the firing shaft 371 and the input shaft 361 is rotated in the first direction, the firing nut 386 is displaced distally toward the end of the end effector 370 to eject the staples 381 from the staple cartridge 380 and incise the tissue. When the firing nut 386 is threadably engaged with the distal threaded portion 397 of the firing shaft 371 and the input shaft 361 is rotated in the second direction, the firing nut 386 is displaced proximally. Once the firing nut 386 threadably re-engages with the proximal thread portion 396 on the firing shaft 371, the proximal advancement of the firing nut 386 slows as it approaches its starting position-due to the smaller or tighter lead of the proximal thread portion 396.

The above being understood, the surgical instrument system 350 employs a rotary driven closure system and firing system that is an improvement over the closure and firing system disclosed in connection with the surgical instrument system of FIGS. 1-5. As will become further apparent as the present Detailed Description proceeds, the closure and firing systems of surgical system 350 serve to positively retain the anvil portion 375 in a closed position during the entire firing cycle or stroke in such a manner as to avoid undesirable "chattering" of the anvil portion during firing.

Referring again to FIGS. 16-18, the closure nut 377 is movable from a proximal, "beginning" position to a distal "ending" position during a clamping stroke in order to move the anvil portion 375 from its open position to its fully-closed position. When the closure nut 377 is in its proximal position, the closure nut 377 is threadably engaged with the threads 372 defined on the input shaft 361. See FIG. 17. As a result of the above, the initial rotation of the input shaft 361 in the first direction can immediately displace the closure nut 377 distally to begin closing the anvil portion 375. As the closure nut 377 moves distally, the closure pins 378 move in the proximal portions 392 of the closure slots 379 until they reach the apex 395 at which point the anvil portion 375 is fully closed or clamped. Continued rotation of the input shaft 361 which is required to distally advance the firing nut 386 will cause the closure nut 377 to continue to advance distally on the input shaft 361. Interaction of the closure pins 378 within the distal slot segments 394 in the anvil portion 375 will retain the anvil portion 375 in the fully-closed position 375 during the completion of the firing stroke.

Notably, further to the above, the rotation of the input shaft 361 being utilized to initiate the clamping stroke of the closure nut 377 is being transferred to the firing shaft 371 via the meshed gears 365 and 385. As the firing shaft 371 is initially rotated, the firing nut 386 is in threaded engagement with the proximal thread portion 396 on the firing shaft 371 which has a tighter or smaller thread lead than the thread lead of the distal thread portion 397. As a result, when the firing nut 386 is in threaded engagement with the proximal thread portion 397, the firing nut 386 moves slowly through a "neutral firing range" designated as "NFR" in FIG. 19. When the firing nut 386 is in the neutral firing range NFR, the firing nut 386 has not advanced distally far enough to start to incise tissue and fire staples. In various arrangements, however, the firing nut 386 may be configured to slidably engage a portion of the anvil portion 375 to positively retain the anvil portion 375 in the closed position and even maintain the spacing of the anvil portion 375 relative to the staple cartridge 380 as the firing nut 386 is advanced distally through the end effector 370. For example, the firing nut 386 may incorporate an I-beam like shape as described in various disclosures that have been herein incorporated by reference that is configured to slidably engage the anvil portion 375. However, because the closure nut 377 maintains a positive closure force on the anvil portion 375, in at least some embodiments, the firing nut 386 is not configured to positively engage the anvil portion 375 so that the firing nut 386 does not apply any closure or clamping motion to the anvil portion.

Referring primarily now to FIGS. 19 and 20, continued rotation of the input shaft 361 and the firing shaft 371 will drive the firing nut 386 to the distal end of the proximal threads 396. Once the drive member 398 on the firing nut 386 engages the distal threads, continued rotation of the firing shaft 377 will result in the distal advancement of the firing nut 386 through the end effector 370. As a result of the above, the clamping operating mode is completed before the actual staple firing mode is commenced. In addition, the anvil portion 375 is positively maintained in the closed position during the entire firing process. Moreover, the surgical instrument system 350 can comprise a sensor system, for example, configured to detect when the staple firing operating mode has been initiated, or is about to be initiated, and pause the electric motor which is driving the input shaft 361. Such a sensor system can be configured to detect the position of the closure nut 377, the firing nut 386, and/or the proximal gear 385 for example. In at least one such instance, the electric motor or other drive actuator arrangement can be paused to allow the surgeon to assess whether they want to proceed with firing the staples into the tissue or re-open the anvil portion 375 to reposition the end effector 370. In at least one instance, the surgeon can be provided with two switches to selectively operate-a first button which will re-start the electric motor and proceed with the firing stroke or a second button which will reverse the electric motor to re-open the anvil portion 375, for example. The first button can be green, for example, and the second button can be red, for example. The first button can include indicia such as "GO FORWARD" thereon while the second button can have other indicia such as "GO BACK" thereon, for example. Such switches can be positioned on a remote control console and/or the handle of the surgical instrument, depending on the circumstances.

Figure 21:
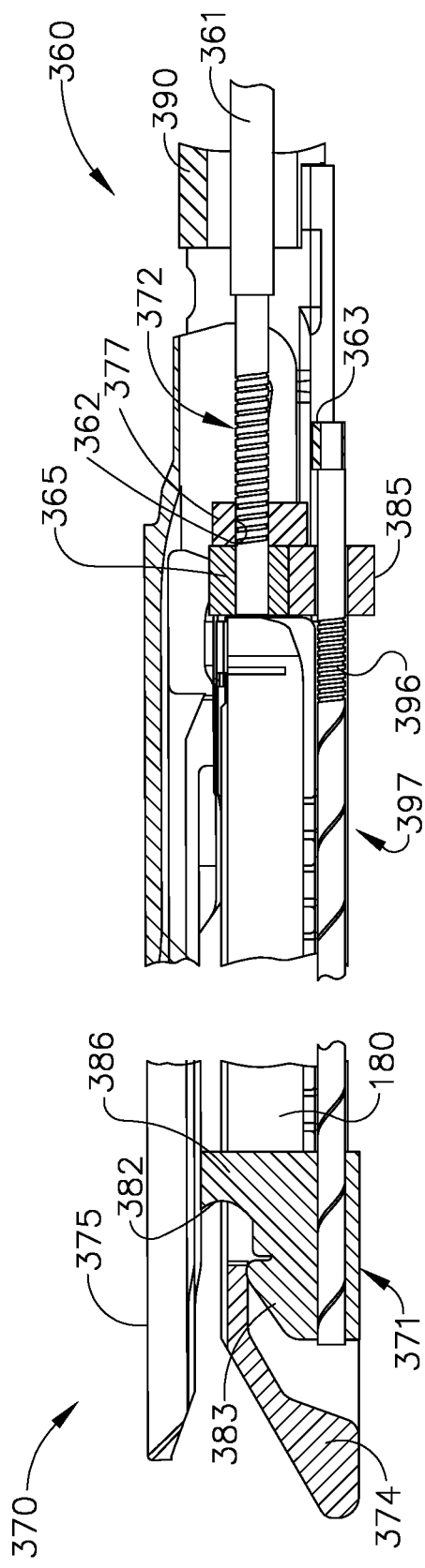
FIG. 21 is another longitudinal cross-sectional view of a portion of the end effector of FIG. 19 with the firing nut located at an end position after the staples have been fired from the staple cartridge with a portion of the anvil shown in cross-section.
Figure 22:
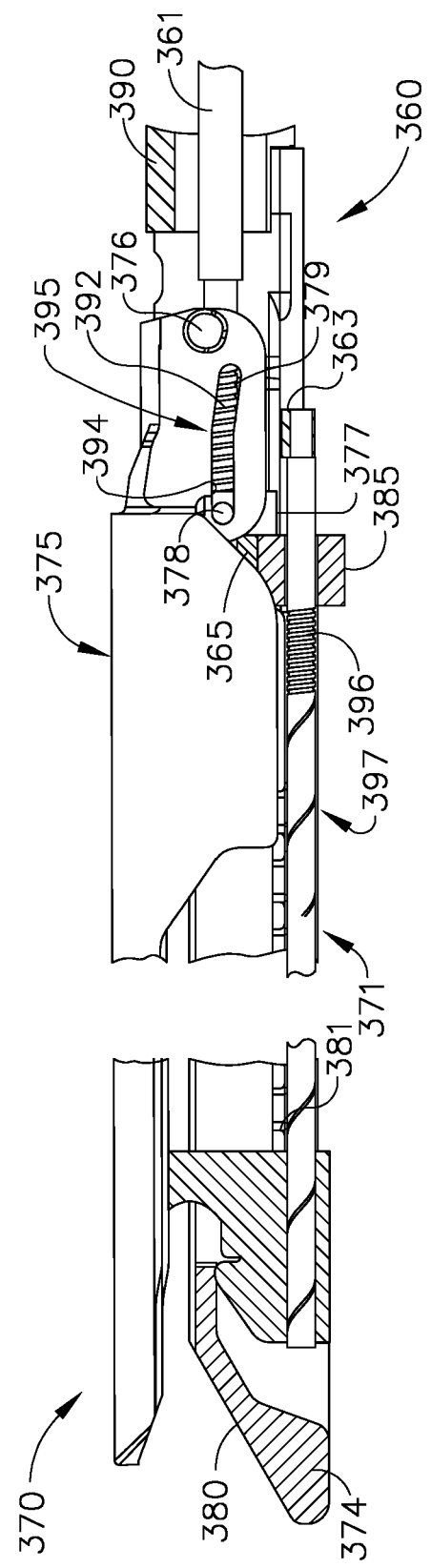
FIG. 22 is another longitudinal cross-sectional view of a portion of the end effector of FIG. 21 with the anvil portion shown in full view.

As described above, the firing nut 386 is advanced distally to eject the staples 81 from the staple cartridge 380. The firing nut 386 can be advanced to the distal end of the end effector 370 to complete a firing stroke, as illustrated in FIGS. 21 and 22. The distal thread portion 397 on the firing shaft 371 can be configured such that the drive member 398 in the firing nut 386 remains threadably engaged with the distal threads 397 on the firing shaft 371 when the firing nut 386 reaches the end of its firing stroke. In at least one such instance, the firing nut 386, the drive member 398, the wedges 383, and/or the cutting member 382 can change the state of a switch positioned at the distal end of the end effector 370 when the firing nut 386 reaches the end of its firing stroke. The switch is in communication with the controller of the surgical instrument system 350 which can reverse the direction of the electric motor to rotate the input shaft 361 in its second direction when the state of the switch is reversed. When the input shaft 361 is rotated in its second direction, the firing nut 386 is retracted toward its unfired position. In addition to or in lieu of the above, the surgical instrument 350 can include a switch which can be actuated by the surgeon to stop and/or reverse the direction of the electric motor.

In use, the anvil portion 375 can be moved away from its fully clamped position to release the tissue captured between the anvil portion 375 and the staple cartridge 380. Moreover, the anvil portion 375 may be moved between its open position and its closed position to clamp and release tissue, as needed, and/or to position the anvil portion 375 relative to the staple cartridge 380 such that the end effector 370 can be inserted into a patient through a trocar, for example. The pause feature described above can allow the surgical instrument system 350 to be operated in a first operating range to open and close the anvil portion 375 without firing the staples in the staple cartridge 380 and/or incising the tissue.

A portion of another shaft assembly 460 that may be employed in connection with the various end effectors disclosed above is illustrated in FIGS. 23-28. As can be seen in those Figures, the shaft assembly 460 includes a threaded rotary input shaft 461. The threaded rotary input shaft 461 is configured to receive rotary input motion from a motor that is located in a handle or housing that is attached to the shaft assembly 460 or a portion of a robotic system that is attached to the shaft assembly 460. In alternative embodiments, the rotary input shaft 461 may be manually actuated by means of a manual trigger or triggers that are supported on a handle from which the shaft assembly 460 protrudes. The shaft assembly 460 includes a hollow outer shaft 510 through which the rotary input shaft 461 extends. A base member 512 is supported in the outer shaft 510 as shown. The base member 512 may be attached to the handle or housing as well as the surgical staple portion of the end effector and effectively function as a "spine" or mechanical "ground" through at least a portion of the shaft assembly 460. The base member 512 also serves as a guide for slidably supporting an actuator member 469 within the outer shaft 510. For example, as can be seen in FIGS. 23-28, the base member 512 comprises an axially extending guide trough 514 for receiving a bottom portion 522 of a guide 520 that is attached to the actuator member 469. When viewed from an end, the guide 520 roughly resembles a "T-shape". As shown, one side of the base member 512 comprises a lateral guide slot 516 for receiving a lateral arm portion 524 of the guide 520.

Figure 25:
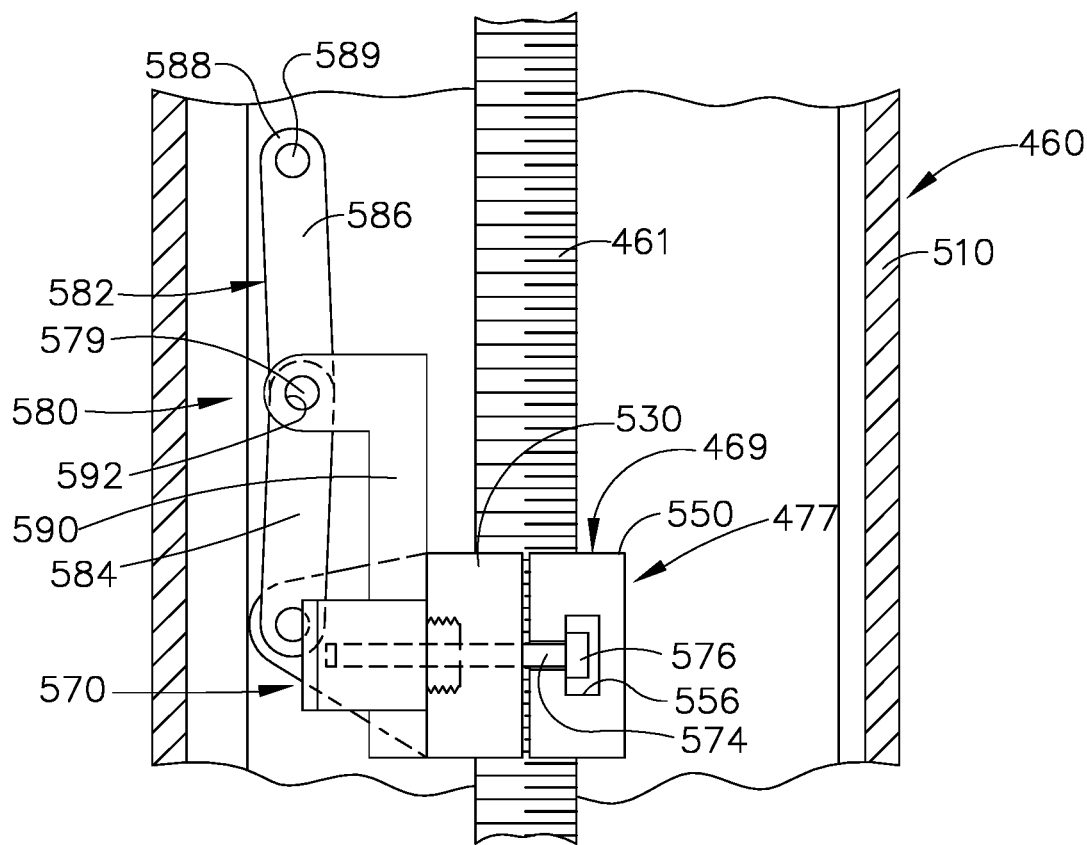
FIG. 25 is another partial cross-sectional top view of the shaft assembly of FIGS. 23 and 24 illustrating the locking system thereof in a "pre-lock configuration"
Figure 26:
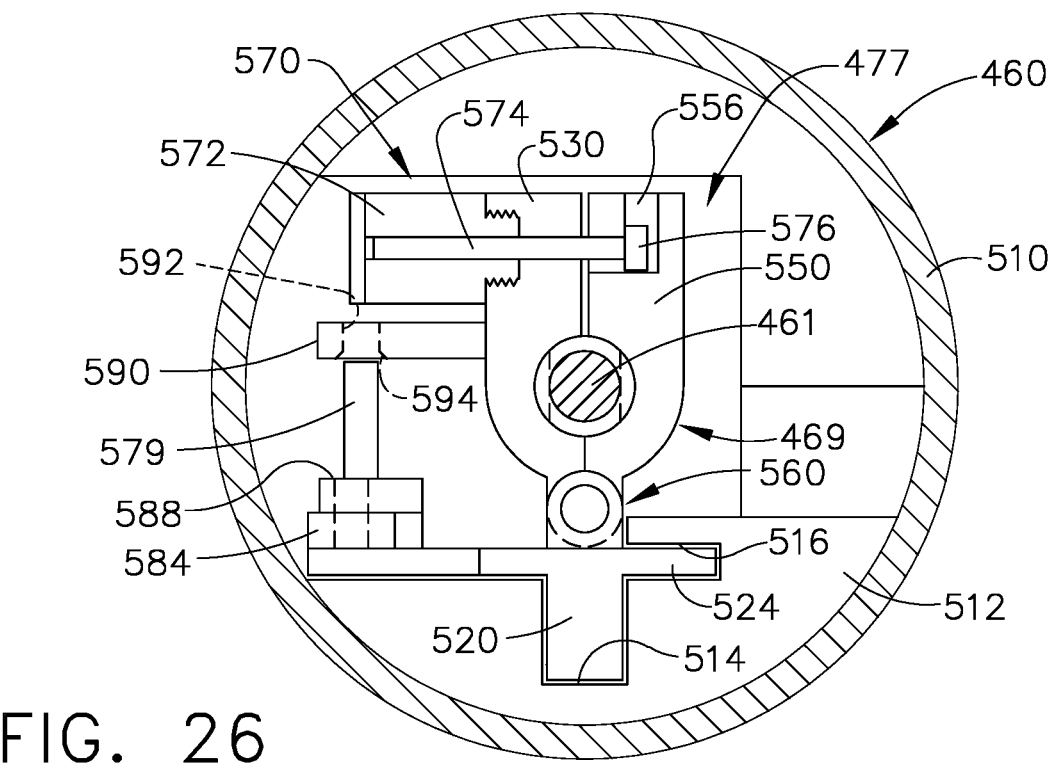
FIG. 26 is a partial cross-sectional elevational view of the shaft assembly of FIG. 25.
Figure 27:
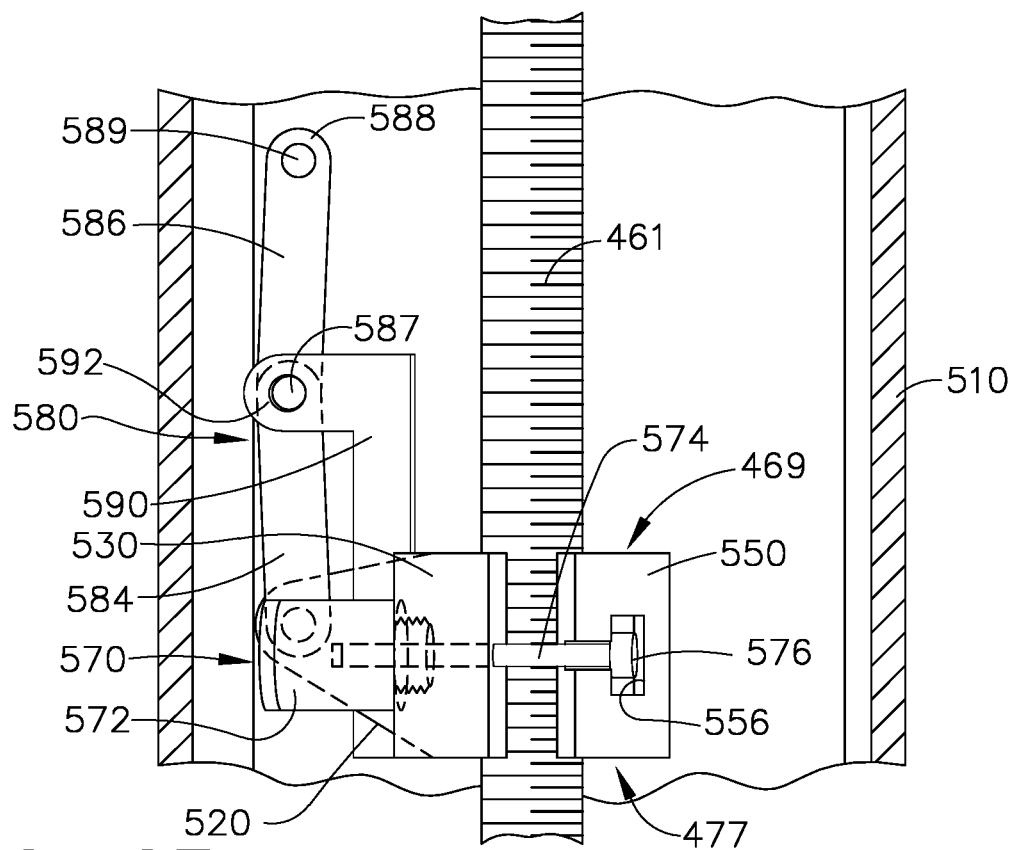
FIG. 27 is another partial cross-sectional top view of the shaft assembly of FIGS. 23-26 with the actuator member in the disengaged configuration and the lock system in a locked configuration.
Figure 28:
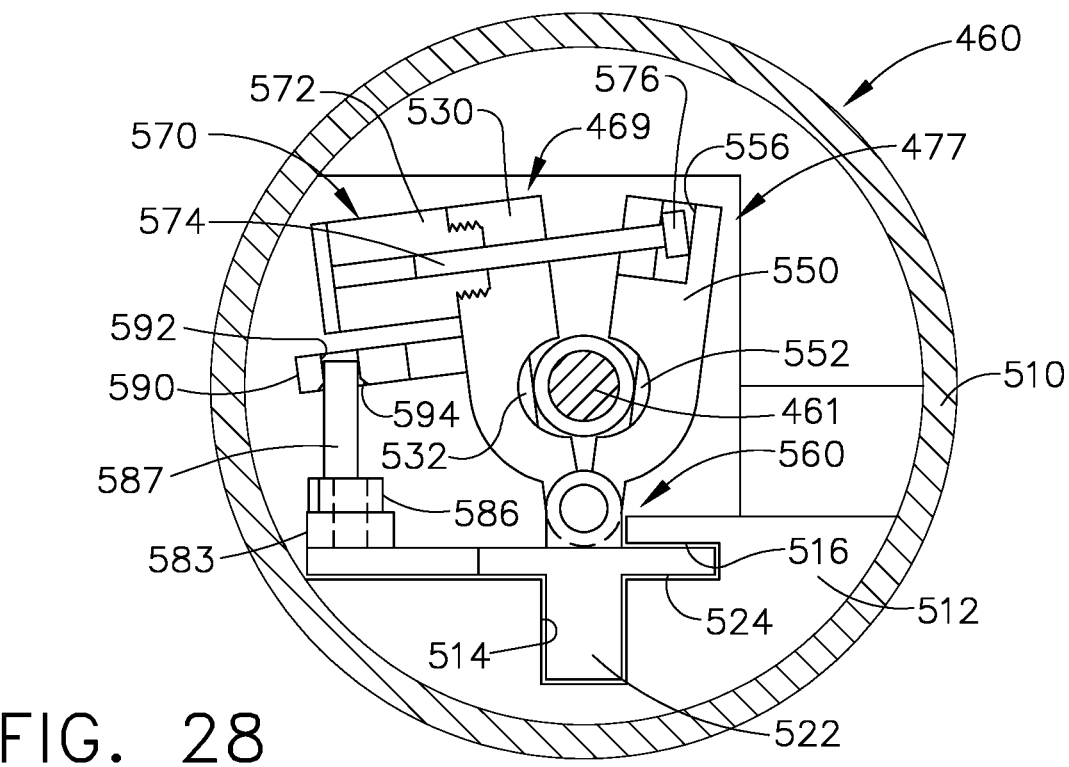
FIG. 28 is a partial cross-sectional elevational view of the shaft assembly of FIG. 27.

As shown in FIGS. 23-28, the actuator member 469 comprises a closure nut assembly 477 that is configured to impart opening and closing motions to an anvil portion in the manner described herein. The closure nut assembly 477 comprises a "clam-shell" arrangement comprising a first closure nut segment 530 and a second closure nut segment 550 that are pivotably supported on a pivot rod or pivot member 560 that is attached to the guide 520. Such arrangement enables the closure nut segments 530, 550 to pivot from an engaged configuration (FIGS. 23-26) to a disengaged configuration (FIGS. 27 and 28). The first closure nut segment 530 includes a first thread engagement member 532 and the second closure nut segment 550 includes a second thread engagement member 552. When the closure nut assembly 477 is in the engaged configuration, the first thread engagement member 532 and the second thread engagement member 552 engage the input shaft 461 such that rotation of the input shaft 461 results in the axial movement of the closure nut assembly 477. It will be appreciated that one, and preferably two, laterally extending pivot pins are attached to a structure that extends from the guide 520 and or the pivot member 560 and are received in the corresponding anvil slots in the manners described above. Thus, axial movement of the closure nut assembly 477 will result in the opening and closing of the anvil portion in the manners described above.

Figure 23:
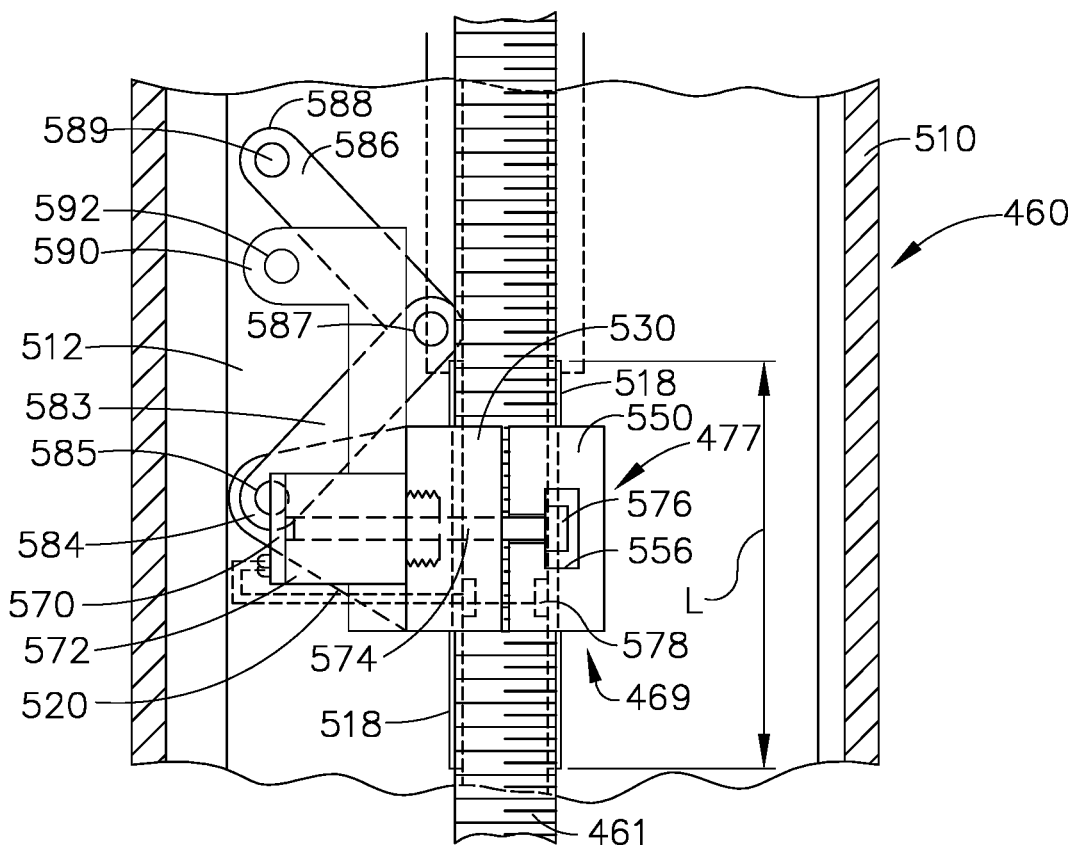
FIG. 23 is a partial cross-sectional top view of a portion of a shaft assembly of a surgical instrument with the actuator member thereof in an engaged configuration.
Figure 24:
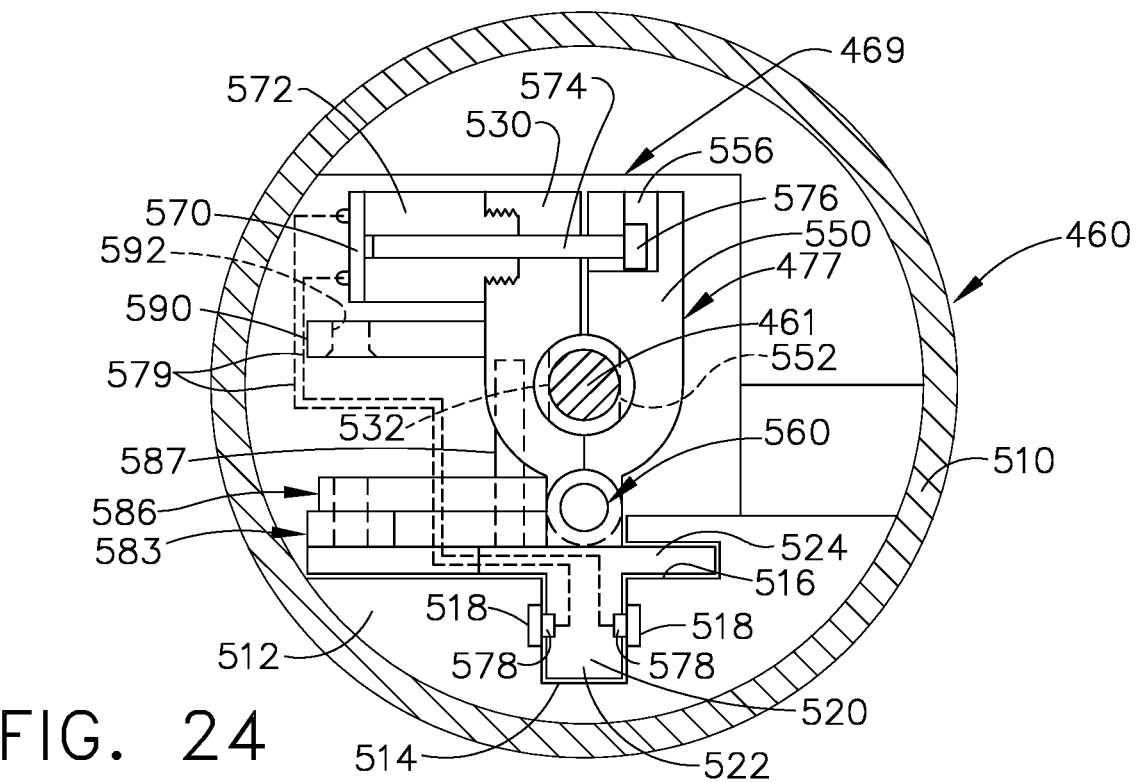
FIG. 24 is another partial cross-sectional elevational view of the shaft assembly of FIG. 23.

Referring to FIGS. 23 and 24, the selective movement of the first and second closure nut segments 530 and 550 between the engaged and disengaged configurations is controlled by a solenoid or switching member 570. In the illustrated arrangement, for example, the solenoid 570 includes a solenoid body portion 572 that is attached to the first closure nut segment 530. A solenoid rod 574 is movably supported within the body portion 572 and the first closure nut segment 530 to be movably received in the second closure nut segment 550. As can be seen in FIGS. 23-28, the solenoid rod 574 has a head 576 that is movably received in U-slot 556 in the second closure nut portion 550.

Still referring to FIGS. 23 and 24, a pair of base contacts 518 are located in the base member 512 and open into the guide trough 514 to facilitate sliding electrical contact with solenoid contacts 578. The base contacts 518 are electrically coupled to a controller by leads 519 that extend through the base member 512 back to the handle, housing or other portion for the robotic system whichever the case may be. For example, the controller may cooperate with a trigger or other switching mechanism that can be used to control the supply of electrical current to the base contacts 518 and ultimately to the solenoid 570 through leads 579 that extend between the solenoid 570 and the solenoid contacts 578. As can be seen in FIG. 23, in at least one arrangement, the range of axial movement of the closure nut assembly 477 may be defined by the length "L" of the base contacts 518, for example. In one arrangement, the solenoid 570, in a de-energized state, is biased into the engaged position wherein the solenoid rod 572 is retained in the retracted state shown in FIGS. 23-26. When the solenoid 570 is energized, the solenoid rod 572 is laterally displaced toward the second closure nut segment 550 to thereby pivot the closure nut assembly 477 to the disengaged configuration (FIGS. 27 and 28). In alternative arrangements, the solenoid may be biased into the disengaged configuration when the solenoid is de-energized and then is moved to the engaged configuration when the solenoid is energized. In still other arrangements, the solenoid must be positively actuated between the engaged and disengaged configurations (i.e., no biasing member is employed in the solenoid to bias the solenoid into one of the described configurations).

When the closure nut assembly 477 is in the disengaged configuration, rotation of the input shaft 461 will not be transferred to the closure nut assembly 477. Thus, in one arrangement, the closure nut 477 may be configured in the engaged position to close the anvil portion. Once the anvil portion has been moved to the closed position (which may be detected by sensors in the anvil portion and or the surgical staple portion), the controller may then de-energize the motor as well as the solenoid which will to move the closure nut assembly 477 to the disengaged configuration. At that point, the controller may once again activate the motor to rotate the input shaft 461 to commence the firing operation in the above-described manner without actuating or axially moving the closure nut assembly 477.

The illustrated surgical instrument system depicted in FIGS. 23-28 also employs a locking system 580 to positively lock the closure nut assembly in position (e.g., prevent further axial movement) when it is in the distal-most disengaged orientation. As can be seen in those Figures, the locking system 580 comprises a movable lock linkage 582 that includes a distal link 583 that is pivotally pinned to a proximal link 586 by an upstanding central lock pin 587. A proximal end 588 of the proximal link 586 is pivotally pinned to the base member 512 by a proximal pin 589. The distal end 584 of the distal link 583 is pivotally pinned to the guide 520 by a pin 585. Thus, the lock linkage 582 moves between a collapsed configuration (FIG. 23), an aligned "pre-locked" configuration (FIGS. 25 and 26) and a locked configuration (FIGS. 27 and 28).

As can be seen in FIGS. 23-28, the locking system 580 also comprises a lock arm 590 that is attached to or otherwise protrudes from the closure nut assembly 477 and, in the illustrated embodiment, from the first closure nut segment 530. The lock arm 590 includes a lock pin hole 592 that is configured to retainingly engage and receive a portion of the lock pin 587 therein. As can be seen in FIGS. 24, 26 and 28, the bottom end of the lock pin hole 592 includes a chamfer or tapered portion 594 to facilitate entry of the lock pin 587 therein.

One method of using the closure nut assembly 477 will now be described. When the clinician desires to close the anvil portion, the input shaft 461 is rotated in a first direction. This rotary motion may be applied to the input shaft 461 by an electric motor, a robotic system or a manually actuatable closure system that is configured to generate rotary motions upon ratcheting or other form of manipulation of a closure trigger or the like. When in that position, the solenoid is biased into the engaged position (by a spring or other biasing arrangement) and remains un-energized. Rotation of the input shaft 461 causes the closure nut assembly 477 to move distally. As was discussed above, the distal movement of the closure nut assembly 477 will result in the closure of the anvil portion by means of the camming interaction between the closure pins and the anvil slots provided in the anvil mounting portion. If the clinician desires to reopen the anvil portion (to reposition the end effector on the desired target tissue or for some other reason), the clinician simply causes the motor or other actuation mechanism to reverse the direction in which the input shaft is rotated (second direction). In any event, once the closure nut assembly 477 has been distally advanced to the position in which the anvil portion is "fully closed" (FIG. 25), the application of the rotary motion to the input shaft 461 is discontinued. This may be manually accomplished by the clinician or, if sensors are employed to detect the position of the closure nut assembly 477 and/or the position of the anvil portion, the control system may "automatically" discontinue application of power to the motor. As can be seen in FIG. 25, when in that fully-closed position, the movable lock linkage is configured in a pre-locked position wherein the end of the lock pin 587 is aligned with the lock hole 592 in the lock arm 590. When in this position, if the clinician desires to open the anvil portion, the motor is simply re-energized to rotate the input shaft 461 in the second direction. If, however, the clinician does not want to reopen the anvil portion and desires to commence the firing stage, the clinician energizes the solenoid to move the closure nut segments to the disengaged configuration (FIGS. 27 and 28). As can be seen in those Figures, when the first closure nut segment 530 is pivoted in the direction of the closure linkage 580, the end of the closure pin 587 enters the hole 592 in the lock arm 590 to positively retain the closure nut assembly 477 in the disengaged position as well as preventing the closure nut assembly 477 from moving axially during the firing sequence. When in that position, as can be seen in FIG. 27, the links 586 and 584 are in a "buckled" configuration and may abut a portion of the base member and/or inner wall of the outer shaft 510 to add further locking resistance to the closure nut assembly 477. In another arrangement, the control system may "automatically" energize the solenoid 570 when the switching system confirmed that the closure nut assembly 477 and/or the anvil portion has attained the fully closed position. In such case, the closure nut assembly 477 is automatically moved to the disengaged and locked position. Once the firing nut has completed the firing stroke and returned to the start position, switches may be employed to detect its status/position and cause the control system to de-energize the solenoid to permit it to be biased back into the engaged position. Other solenoid arrangements may not include a biasing member to bias the solenoid back to its starting position, but instead require a second signal to move it back to the starting position. In those cases, the control system would send the second signal to the solenoid to cause the closure nut assembly to reengage the input shaft. Thereafter, the control system may automatically energize the motor to rotate the input shaft in the second direction to return the closure nut assembly to its beginning position and thereby return the anvil portion to the open position.

The surgical instrument systems described herein are motivated by an electric motor; however, the surgical instrument systems described herein can be motivated in any suitable manner. In various instances, the surgical instrument systems described herein can be motivated by a manually-operated trigger, for example.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The surgical instrument systems described herein are motivated by one or more electric motors; however, the surgical instrument systems described herein can be motivated in any suitable manner. In various instances, the surgical instrument systems described herein can be motivated by a manually-operated trigger, for example.

Examples

Example 1—A surgical instrument, comprising a rotary input shaft and means for selectively applying rotary input motions to the rotary input shaft. The surgical instrument further comprises a surgical end effector that comprises a first jaw and a second jaw that is selectively movable relative to the first jaw between an open and closed position. A firing shaft operably interfaces with the rotary input shaft such that the firing shaft rotates in response to rotation of the rotary input shaft. A firing member is movably supported in one of the first and second jaws for selective axial movement between start and end positions in response to rotation of the firing shaft. A closure member is located in threaded engagement with the rotary input shaft such that rotation of the rotary input shaft in a first direction causes the closure member to move the second jaw to the closed position. The closure member remains in threaded engagement with the rotary input shaft to retain the second jaw in the closed position while continued rotation of the rotary input shaft in the first direction drives the firing member from the start position to the end position.

Example 2—The surgical instrument of Example 1, wherein the first jaw comprises a surgical staple cartridge and the second jaw comprises an anvil, and wherein the firing member comprises a tissue cutting surface and a wedge for driving surgical staples from the surgical staple cartridge into forming contact with the anvil.

Example 3—The surgical instrument of Examples 1 or 2, wherein the input shaft and the firing shaft are not coaxially aligned.

Example 4—The surgical instrument of Examples 1, 2 or 3, wherein the firing shaft comprises a proximal set of threads having a first lead and a distal set of threads having a second lead that differs from the first lead.

Example 5—The surgical instrument of Example 4, wherein the second lead is greater than the first lead.

Example 6—The surgical instrument of Examples 2, 3, 4 or 5, wherein the firing member is configured to engage the anvil as the firing member moves between the start and end positions.

Example 7—The surgical instrument of Examples 1, 2, 3, 4, 5 or 6, wherein the firing member is configured to space the first and second jaws at a desired distance from each other as the firing member moves between the start and end positions.

Example 8—The surgical instrument of Examples 1, 2, 3, 4, 5, 6 or 7, wherein the means for selectively applying comprises an electric motor.

Example 9—The surgical instrument of Examples 1, 2, 3, 4, 5, 6 or 7, wherein the means for selectively applying comprises a robotic system.

Example 10—A surgical instrument, comprising an elongate shaft assembly that comprises an input shaft. The surgical instrument further comprises a surgical end effector that comprises a staple cartridge portion and an anvil that is supported for selective movement relative to the staple cartridge portion. A firing shaft is operably supported by the staple cartridge portion. The firing shaft operably interfaces with the input shaft such that the firing shaft is actuated upon application of an actuation motion to the input shaft. A firing member is movably supported in the staple cartridge portion for selective axial movement between start and end positions in response to the actuation of the firing shaft. A closure member operably interfaces with the input shaft and is configured to axially move from a beginning position to an ending position. A clamped position is located intermediate the beginning and ending positions and corresponds to a position wherein the closure member retains the anvil in a fully closed position. Further actuation of the input shaft after the closure member has attained the clamping position causes the firing member to move from the start to the end position and the closure member to move from the clamping position to the ending position while retaining the anvil in the fully closed position.

Example 11—The surgical instrument of Example 10, wherein the closure member includes at least one pivot pin that is received in a corresponding pin slot in a mounting portion of the anvil portion. Each pin slot comprises a proximal slot portion that corresponds to the beginning position of the closure member. A distal slot portion joins the proximal slot portion at an apex point that corresponds to the clamped position such that the distal slot portion is not axially aligned with the proximal slot portion.

Example 12—The surgical instrument of Examples 10 or 11, wherein the firing shaft is rotatably actuated by applying the actuation motion to the input shaft and wherein the firing member is threadably engaged with the firing shaft.

Example 13—The surgical instrument of Examples 10, 11 or 12, wherein the input shaft and the firing shaft are not coaxially aligned.

Example 14—The surgical instrument of Examples 10, 11, 12 or 13, wherein the firing shaft comprises a proximal set of threads having a first lead and a distal set of threads having a second lead that differs from the first lead.

Example 15—The surgical instrument of Example 14, wherein the second lead is greater than the first lead.

Example 16—The surgical instrument of Examples 10, 11, 12, 13, 14 or 15, wherein the closure member is threadably engaged with the input shaft.

Example 17—The surgical instrument of Examples 10, 11, 12, 13, 14, 15 or 16, further comprising means for applying the actuation motion to the input shaft.

Example 18—The surgical instrument of Example 17, wherein the means for applying comprises an electric motor.

Example 19—The surgical instrument of Example 17, wherein the means for applying comprises a robotic system.

Example 20—A surgical instrument system, comprising a housing and a motor that is operably supported by the housing and configured to generate rotary motions. A rotary input shaft is configured to receive the rotary motions from the motor. The surgical instrument system further comprises a surgical end effector that comprises a staple cartridge portion and an anvil that is supported for selective movement relative to the staple cartridge portion. A firing shaft is operably supported by the staple cartridge portion. The firing shaft operably interfaces with the input shaft such that the firing shaft is actuated upon application of the rotary motions to the rotary input shaft. The surgical end effector further comprises a firing nut that comprises a tissue cutting surface and a wedge. The firing nut is in threaded engagement with a threaded section of the firing shaft that comprises a proximal thread segment that comprises a first thread lead and a distal thread segment that comprises a second thread lead that is greater than the first thread lead. The surgical instrument system further comprises a closure nut that is in threaded engagement with the rotary input shaft such that rotation of the rotary input shaft in a first direction causes the closure nut to move the anvil from an open to a closed position. The closure nut remains in threaded engagement with the rotary input shaft to retain the anvil in the closed position while continued rotation of the rotary input shaft in the first direction drives the firing nut from threaded engagement with the proximal thread segment to threaded engagement with the distal thread segment.

Example 21—A surgical instrument, comprising a surgical end effector and a threaded rotary input shaft. An actuator member is in operable engagement with the surgical end effector and is in selective threaded engagement with the threaded rotary input shaft such that when the actuator member is in an engaged configuration, the actuator member is in threaded engagement with the threaded rotary input shaft such that rotation of the threaded rotary input shaft causes the actuator member to move axially to impart an actuation motion to the surgical end effector and when the actuator member is in a disengaged configuration, rotation of the threaded rotary input shaft will not be imparted to the actuator member. The surgical instrument further comprises means for selectively moving the actuator between the engaged and disengaged configurations and a locking system for preventing axial movement of the actuator member when the actuator member is in the disengaged configuration.

Example 22—The surgical instrument of Example 21, wherein the surgical end effector comprises a first jaw and a second jaw that is selectively movable relative to the first jaw between an open and closed position. The actuator member comprises a closure member that is in operable engagement with the second jaw such that when the closure member is in the engaged configuration, rotation of the threaded rotary input shaft causes the closure member to move the second jaw from the open to the closed position and when the threaded rotary input shaft is rotated in a second direction, the closure member moves the second jaw from the closed position to the open position.

Example 23—The surgical instrument of Example 22, wherein the first jaw comprises a surgical staple cartridge and the second jaw comprises an anvil.

Example 24—The surgical instrument of Examples 21, 22 or 23, wherein the actuator member comprises a first actuator segment that is supported for axial travel relative to the threaded rotary input shaft and comprises a first thread engagement portion. A second actuator segment is supported for axial travel relative to the threaded rotary input shaft and comprising a second thread engagement portion. The first and second actuator segments are selectively movable relative to each other by the means for selectively moving between the engaged configuration wherein the first and second thread engagement portions cooperate to threadably engage the threaded rotary input shaft and the disengaged configuration wherein the first and second thread engagement portions do not threadably engage the threaded rotary input shaft.

Example 25—The surgical instrument of Example 24, wherein the first actuator segment and the second actuator segment are pivotally coupled together, and wherein the means for selectively moving comprises a solenoid.

Example 26—The surgical instrument of Examples 24 or 25, wherein the locking system comprises a locking pin that is movably supported relative to the actuator member and a lock member that protrudes from the first actuator segment and is configured to lockingly engage the locking pin when the first actuator segment is in the disengaged configuration.

Example 27—The surgical instrument of Examples 21, 22, 23, 24, 25 or 26, wherein the surgical instrument further comprises means for selectively applying rotary input motions to the threaded rotary input shaft.

Example 28—The surgical instrument of Example 27, wherein the means for selectively applying comprises an electric motor.

Example 29—The surgical instrument of Examples 21, 22, 23, 24, 25, 26, 27 or 28, wherein the means for selectively applying comprises a robotic system.

Example 30—The surgical instrument of Examples 22, 23, 24, 25, 26, 27, 28, 29 further comprising a firing shaft that operably interfaces with the threaded rotary input shaft such that the firing shaft rotates in response to rotation of the threaded rotary input shaft. A firing member is movably supported in one of the first and second jaws for selective axial movement between start and end positions in response to rotation of the firing shaft.

Example 31—The surgical instrument of Example 30, wherein the first jaw comprises a surgical staple cartridge and the second jaw comprises an anvil, and wherein the firing member comprises a tissue cutting surface and a wedge for driving surgical staples from the surgical staple cartridge into forming contact with the anvil.

Example 32—A surgical instrument comprising a rotary input shaft and a surgical end effector. The surgical end effector comprises a first jaw and a second jaw that is selectively movable relative to the first jaw between an open and closed position. The surgical instrument further comprises a closure member that is in operable engagement with the second jaw and in selective operable engagement with the rotary input shaft such that when the closure member is in an engaged configuration with the rotary input shaft, rotation of the rotary input shaft causes the closure member to impart an actuation motion to the second jaw and when the closure member is in a disengaged configuration, rotation of the input shaft will not be imparted to the closure member. The surgical instrument further comprises a switch for selectively moving the closure member between the engaged and disengaged configuration and a locking system for preventing axial movement of the closure member when the closure member is in the disengaged configuration.

Example 33—The surgical instrument of Example 32, wherein the first jaw comprises a surgical staple cartridge and the second jaw comprises an anvil.

Example 34—The surgical instrument of Examples 32 or 33, wherein the closure member comprises a first closure nut segment that is supported for axial travel relative to the rotary input shaft and comprises a first thread engagement portion. A second closure nut segment is supported for axial travel relative to the rotary input shaft and comprises a second thread engagement portion. The first and second closure nut segments are selectively movable relative to each other by the switch between the engaged configuration wherein the first and second thread engagement portions cooperate to threadably engage the rotary input shaft and the disengaged configuration wherein the first and second thread engagement portions do not threadably engage the rotary input shaft.

Example 35—The surgical instrument of Example 34, wherein the first closure nut segment and the second closure nut segment are pivotally coupled together, and wherein the switch comprises a solenoid.

Example 36—The surgical instrument of Examples 32, 33, 34 or 35, wherein the locking system comprises a locking pin supported relative to the closure member and a lock member that protrudes from a portion of the first closure member and is configured to lockingly engage the locking pin when the closure member is in the disengaged configuration.

Example 37—The surgical instrument of Example 36, wherein the locking pin is movably supported relative to the closure member.

Example 38—The surgical instrument of Example 37, wherein the locking pin is supported on a linkage that is movably coupled to the closure member.

Example 39—The surgical instrument of Examples 32, 33, 34, 35, 36, 37 or 38 further comprising a firing shaft that operably interfaces with the rotary input shaft such that the firing shaft rotates in response to rotation of the rotary input shaft and a firing member that is movably supported in one of the first and second jaws for selective axial movement between start and end positions in response to rotation of the firing shaft.

Example 40—A surgical instrument system, comprising a surgical end effector and a threaded rotary input shaft. The surgical instrument further comprises a clam-shell actuator member that is supported in operable engagement with the surgical end effector and is selectively movable between a first closed configuration wherein the actuator member is in threaded engagement with the rotary input shaft and a second open configuration wherein the actuator member is not in threaded engagement with the threaded rotary input shaft.

Example 41—A staple cartridge for use with a surgical stapler including an anvil, the staple cartridge comprising a cartridge body including a proximal end, a distal end, a deck, a longitudinal slot defined in the deck, and a longitudinal row of staple cavities. The staple cartridge further comprises staples removably stored in the longitudinal row of staple cavities, a longitudinal row of staple drivers movable between an unfired position and a fired position to drive the staples toward the anvil, and a firing system movable toward the distal end to sequentially move the staple drivers between their unfired position and their fired position. The longitudinal row of staple drivers comprises a first staple driver comprising a first bottom drive surface configured to be driven by the firing system and a first support surface configured to drive a first staple toward the anvil, wherein a first driver distance is defined between the first bottom drive surface and the first support surface and a second staple driver comprising a second bottom drive surface configured to be driven by the firing system and a second support surface configured to drive a second staple toward the anvil, wherein a second driver distance is defined between the second bottom drive surface and the second support surface, and wherein the second driver distance is different than the first driver distance.

Example 42—The staple cartridge of Example 41, wherein the first staple driver is positioned proximally with respect to the second staple driver, and wherein the first driver distance is shorter than the second driver distance.

Example 43—The staple cartridge of Examples 41 or 42, wherein the first support surface comprises a first cradle configured to receive a portion of the first staple therein, and wherein the second support surface comprises a second cradle configured to receive a portion of the second staple therein.

Example 44—The staple cartridge of Examples 41, 42, or 43, wherein the first staple driver is not connected to the second staple driver.

Example 45—The staple cartridge of Examples 41, 42, or 43, wherein the first staple driver is connected to the second staple driver.

Example 46—The staple cartridge of Examples 41, 42, 43, 44, or 45, wherein the longitudinal row of staple drivers comprises a third staple driver positioned distally with respect to the second staple driver, wherein the third staple driver comprises a third bottom drive surface configured to be driven by the firing system and a third support surface configured to drive a third the staple toward the anvil, wherein a third driver distance is defined between the third bottom drive surface and the third support surface, and wherein the second driver distance is shorter than the third driver distance.

Example 47—The staple cartridge of Examples 41, 42, 43, 44, 45, or 46, wherein the first driver height, the second driver height, and the third driver height increase in height according to a linear gradient.

Example 48—The staple cartridge of Examples 41, 42, 43, 44, 45, or 46, wherein the first driver height, the second driver height, and the third driver height increase in height according to a geometric gradient.

Example 49—The staple cartridge of Examples 41, 42, 43, 44, 45, 46, 47, or 48, wherein the first longitudinal row of staple drivers are configured to drive a first group of the staples, wherein the first staple and the second staple are part of the first group of staples, wherein the staple cartridge further comprises a second longitudinal row of staple drivers configured to drive a second group of the staples, wherein the first group of staples are defined by a first undeformed height and the second group of staples are defined by a second undeformed height, and wherein the first undeformed height is different than the second undeformed height.

Example 50—The staple cartridge of Example 49, wherein the deck comprises a first step aligned with the first group of staples and a second step aligned with the second group of staples, wherein the first step is defined by a first height, wherein the second step is defined by a second height, and wherein the first height is different than the second height.

Example 51—The staple cartridge of Examples 41, 42, 43, 44, 45, 46, 47, 48, or 49, wherein the deck is flat.

Example 52—The staple cartridge of Examples 41, 42, 43, 44, 45, 46, 47, 48, 49, 50 or 51, wherein the staples are positioned below the deck when the staple drivers are in their unfired position.

Example 53—The staple cartridge of Examples 41, 42, 43, 44, 45, 46, 47, 48, 49, 50, 51, or 52 further comprising a piece of adjunct material positioned over the deck.

Example 54—The staple cartridge of Example 53, wherein the adjunct material comprises a tissue thickness compensator.

Example 55—The staple cartridge of Examples 41, 42, 43, 44, 45, 46, 47, 48, 49, 50 or 51, wherein the first staple is positioned below the deck and the second staple is partially positioned above the deck when the staple drivers are in their unfired position, wherein the staple cartridge further comprises an adjunct material positioned over the deck, and wherein the second staple is partially embedded in the adjunct material when the staple drivers are in their unfired position.

Example 56—The staple cartridge of Example 55, wherein the adjunct comprises a tissue thickness compensator.

Example 57—The staple cartridge of Examples 41, 42, 43, 44, 45, 46, 47, 48, 49, 50 or 51, wherein the staples driven by the longitudinal row of staple drivers are stored within the cartridge body such that they are positioned at the same distance relative to the deck when the staple drivers are in their unfired position.

Example 58—The staple cartridge of Examples 41, 42, 43, 44, 45, 46, 47, 48, 49, 50 or 51, wherein the staples driven by the longitudinal row of staple drivers are stored within the cartridge body such that they are not positioned at the same distance relative to the deck when the staple drivers are in their unfired position.

Example 59—A staple cartridge for use with a surgical stapler including an anvil, the staple cartridge comprising a cartridge body including a proximal end, a distal end, a deck, a longitudinal slot defined in the deck, and a longitudinal row of staple cavities. The staple cartridge further comprises staples removably stored in the longitudinal row of staple cavities, a longitudinal row of staple drivers movable between an unfired position and a fired position to drive the staples toward the anvil, a firing system movable toward the distal end to sequentially move the staple drivers between their unfired position their fired position, and means for driving the staples to different distances relative to the deck.

Example 60—An end effector for use with a surgical system, the end effector comprising a fastener cartridge including a distal end, a deck, and a longitudinal row of fastener cavities. The end effector further comprises fasteners removably stored in the longitudinal row of fastener cavities, a forming jaw, a longitudinal row of fastener drivers movable between an unfired position and a fired position to drive the fasteners toward the forming jaw, and a firing system movable toward the distal end to sequentially move the fastener drivers between their unfired position and their fired position. The longitudinal row of fastener drivers comprises a first fastener driver comprising a first bottom drive surface configured to be driven by the firing system and a first support surface configured to drive a first fastener toward the anvil, wherein a first driver distance is defined between the first bottom drive surface and the first support surface, and a second fastener driver comprising a second bottom drive surface configured to be driven by the firing system and a second support surface configured to drive a second fastener toward the anvil, wherein a second driver distance is defined between the second bottom drive surface and the second support surface, and wherein the second driver distance is different than the first driver distance.

The Entire Disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719;

U.S. patent application Ser. No. 13/524,049, entitled ARTICULATABLE SURGICAL INSTRUMENT COMPRISING A FIRING DRIVE, filed on Jun. 15, 2012; now U.S. Patent Application Publication No. 2013/0334278;

U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical stapling system, comprising:
   a shaft;
   a closure driver;
   a firing driver comprising a cam; and
   an end effector attached to said shaft, wherein said end effector comprises:
      a first jaw;
      a second jaw movable relative to said first jaw, wherein said second jaw is configured to be moved into a fully clamped position during distal movement of said closure driver through a closure stroke; and
      a staple cartridge comprising a plurality of staples removably stored therein, wherein said staples are configured to be ejected from said staple cartridge toward said second jaw during distal movement of said firing driver through a staple firing stroke, wherein said cam is configured to engage said second jaw during said staple firing stroke, and wherein said firing driver and said closure driver are configured to move distally simultaneously through only a portion of said closure stroke, wherein the portion of said closure stroke begins after said second jaw is in a partially clamped position and prior to said second jaw being moved into said fully clamped position.

2. The surgical stapling system of claim 1, wherein said closure driver comprises a rotary-driven input shaft.

3. The surgical stapling system of claim 1, wherein said firing driver comprises a rotary-driven input shaft.

4. The surgical stapling system of claim 1, wherein said closure driver is configured to cam said second jaw toward said first jaw upon distal movement thereof.

5. The surgical stapling system of claim 1, wherein said closure driver is movable relative to said firing driver during a portion of said closure stroke.

6. A surgical stapling assembly, comprising:
   a first jaw;
   a second jaw movable relative to said first jaw;
   a closure driver actuatable to move said second jaw into a fully clamped position during distal movement of said closure driver through a closure stroke, wherein said closure driver comprises a first cam configured to engage said second jaw during said closure stroke; and
   a firing driver actuatable distally through a firing stroke, wherein said firing driver comprises a second cam configured to engage said second jaw during said firing stroke, and wherein said closure driver and said firing driver are simultaneously movable distally during only a portion of said closure stroke that beings after said second jaw being moved into a partially clamped position and prior to said second jaw being moved into said fully clamped position.

7. The surgical stapling assembly of claim 6, further comprising a staple cartridge comprising a plurality of staples removably stored therein, wherein said staples are configured to be ejected from said staple cartridge based on said firing driver moving through said firing stroke.

8. The surgical stapling assembly of claim 6, wherein said closure driver is movable relative to said firing driver during a portion of said closure stroke.

9. The surgical stapling assembly of claim 6, wherein said closure driver comprises a threaded aperture.

10. The surgical stapling assembly of claim 9, wherein said closure driver is movable relative to said firing driver during a portion of said closure stroke.

11. The surgical stapling assembly of claim 9, further comprising a staple cartridge comprising a staple, wherein said firing driver comprises a wedge to deploy said staple from said staple cartridge during said firing stroke.

12. The surgical stapling assembly of claim 9, wherein said closure driver comprises a threaded aperture.

13. The surgical stapling assembly of claim 9, wherein said firing driver comprises a threaded aperture.

14. The surgical stapling assembly of claim 6, wherein said firing driver comprises a threaded aperture.

15. A surgical stapling assembly, comprising:
   a first jaw;
   a second jaw rotatable relative to said first jaw between an open position and a closed position;
   a closure driver movable through a closure stroke, wherein said closure driver comprises a first cam configured to engage said second jaw during said closure stroke to rotate said second jaw toward said closed position; and
   a firing driver movable through a firing stroke, wherein said firing driver comprises a second cam configured to engage said second jaw during said firing stroke, and wherein said closure driver and said firing driver are simultaneously movable during only a portion of said closure stroke that beings after said second jaw being moved out of said open position and prior to said second jaw being moved into said closed position.

* * * * *